(12) United States Patent
Xie et al.

(10) Patent No.: US 10,499,931 B2
(45) Date of Patent: Dec. 10, 2019

(54) HEMISPHERICAL REAMER HAVING CIRCULAR CUTTING MEMBERS AND METHODS OF MAKING THE SAME

(71) Applicants: Ping Xie, Ashland, MA (US); Xue Li, Ashland, MA (US)

(72) Inventors: Ping Xie, Ashland, MA (US); Xue Li, Ashland, MA (US)

( * ) Notice: Subject to any disclaimer, the term of this patent is extended or adjusted under 35 U.S.C. 154(b) by 382 days.

(21) Appl. No.: 15/412,028

(22) Filed: Jan. 22, 2017

(65) Prior Publication Data

US 2017/0209156 A1    Jul. 27, 2017

Related U.S. Application Data

(60) Provisional application No. 62/286,413, filed on Jan. 24, 2016, provisional application No. 62/310,519, filed on Mar. 18, 2016, provisional application No. 62/446,461, filed on Jan. 15, 2017, provisional application No. 62/448,117, filed on Jan. 19, 2017.

(51) Int. Cl.
| | |
|---|---|
| *A61B 17/16* | (2006.01) |
| *A61F 2/34* | (2006.01) |
| *A61F 2/46* | (2006.01) |
| *A61B 17/32* | (2006.01) |
| *A61B 17/00* | (2006.01) |

(52) U.S. Cl.
CPC ...... *A61B 17/1666* (2013.01); *A61B 17/1617* (2013.01); *A61B 17/32* (2013.01); *A61F 2/34* (2013.01); *A61F 2/46* (2013.01); *A61B 2017/00526* (2013.01)

(58) Field of Classification Search
CPC ............ A61B 17/1666; A61B 17/1617; A61B 17/1684
USPC ................................................. 606/80–81, 91
See application file for complete search history.

(56) References Cited

U.S. PATENT DOCUMENTS

| | | | | |
|---|---|---|---|---|
| 2004/0073224 A1* | 4/2004 | Bauer | ................ | A61B 17/1666 606/81 |
| 2006/0025774 A1* | 2/2006 | Fishbein | ............ | A61B 17/1659 606/81 |
| 2006/0217730 A1* | 9/2006 | Termanini | .......... | A61B 17/1666 606/81 |
| 2010/0076442 A1* | 3/2010 | Xie | ..................... | A61B 17/1666 606/80 |
| 2014/0271005 A1* | 9/2014 | Xie | ..................... | A61B 17/1746 408/1 R |
| 2016/0089158 A1* | 3/2016 | Fortin | ................ | A61B 17/1666 606/81 |

\* cited by examiner

*Primary Examiner* — Matthew J Lawson

(57) ABSTRACT

A spherical reamer comprises a cutting element having a support member and at least one circumference cutting member built on it. The cutting member can be characterized by edge configuration, geometric parameters or further by positional parameters, respectively. All variations of the parameters above lead various types of the cutting elements and methods of including self- assembling and/or "One Size Cutting Element for Assembling Several Size of Reamers" in order to assembling either reusable or disposable reamer.

24 Claims, 14 Drawing Sheets

HEMISPHERICAL REAMER HAVING CIRCULAR CUTTING MEMBERS AND METHODS OF MAKING THE SAME

CROSS-REFERENCE TO RELATED APPLICATION

This application claims the benefit of U.S. Provisional Application No. 62/286,413, filed on Jan. 24, 2016, entitled An Acetabular Reamer With At Least Partial Circumference Cutting Edge; Provisional Application No. 62/310,519, filed on Mar. 18, 2016, entitled A Circular Cutting Member For A Spherical Reamer And Methods Of Making The Same; Provisional Application No. 62/446,461, filed on Jan. 15, 2017, entitled A Cutting Element For Assembling A Hemispherical Reamer And Methods Of Making Both and Provisional Application No. 62/448,117, filed on Jan. 19, 2017, entitled A Hemispherical Reamer Self-Assembled by A Cutting Element And Methods Of Making Both. The entire disclosure of the above applications is incorporated herein by reference.

FIELD OF THE INVENTION

The present invention is especially, but not exclusively, applicable to the field of a hemispherical reamer and a circular cutting element and methods of making both them. The reamer is able to ream at least a partial spherical surface. It is related to orthopedic reamers and other applicable industrial applications, or the like.

BACKGROUND OF THE INVENTION

A hemispherical reamer for reshaping at least partial spherical cavity is widely used in current medical procedures, such as, bone sockets in total hip arthroplasty (THA). A plurality of reamers invented in the past has mostly derived from an idea of "convex-concave match or spherical radius matches" design. The reamers usually comprised of a full hemispheric thin wall shell with a specific radius, a plurality of cutting surfaces projected from and helically distributed on the convex surface of the spherical shell, basically forming a hemispheric "cheese grater". In particular, such the cutting surfaces spirally distributed around the rotational axis of the sphere and created an imaginary cutting profile along the arch of the shell cross section, which has a virtual cutting axis. The cutting axis is vertically (90-degree angle) toward the longitudinal axis of the sphere to be cut. Adjacent each cutting surface, there is opening to form a narrow passage extending from the exterior hemispherical surface into the internal chamber of the cutting shell. In the past decades, only a few alternative designs of such reamer have been developed. The prior art reamers as mentioned have common characteristics as follow:

A limited functioning life of the cutting edge: The projected cutting surfaces are made from flat panel of metal, which were stamped, punched and perforated in order to create cutting surfaces having the desired height, shape, adjacent openings, and a spherical shell. They formed "open mouth" cutting surfaces facing the surface to be cut, positioned at 90-degree angle to the latitude lines of the spherical reamer surface. Actually, under a more detailed study, such processing steps can only form a right angle cliff edge on the cutting surface and it can hardly be sharpened in any manners. This kind of processing steps and design for a cutting surface is quite different from the ideal cutting ware and easily becomes dull at the corner of the cliff edge, if the material used is not hard or thin enough or the punching tool gets dull. In order to increase the sharpness and functioning life of such cutting surface, thinner and harder materials must be used for better outcomes. However, this would increase the cost of the reamer and forming tools.

A limited total edge of cutting exposed to the surface to be cut: In either V or arched-shape of cutting surface in the prior art, only a limited tip section can intimately contact the cutting surface and is to efficiently cut the surface. Other elevated parts of the cutting surface are just support members, not being used for cutting.

Such concerns and some obvious defects of the prior art reamers have been addressed. In U.S. Pat. No. 9,101,368, (Sidebotham et al.), the concept of the functioning life of the reamer was addressed and tested. A useful result reported has shown that average functioning life of the regular cheese grater only lasted 2-6 times of uses on maintaining average bone reaming quality before it begins suboptimal operation. Such variations depend upon the design and manufacturing method of the reamer from the suppliers. There are evidences that the cliff edge of the cutting surface discussed above becomes a round shape very soon after few runs. Unfortunately, Sidebotham et al. was unable to bring a direct solution about improving the dulling problem of the cutting surface. Instead, Sidebotham et al. has adjusted the orientation of some cutting surface in to more efficiently direction of cutting for properly conducting the axial pushing force applied by the surgeon, particularly when the cutting surface is corresponding to cutting the "equatorial zone". In order to avoid the dulling problem of the prior art reamers, one might further reduce either the thickness of the materials used for the reamer or the usage frequency of the reamer. So the concept of a disposable reamer becomes one possible path in public focus.

In U.S. Pat. No. 8,407,880, (Stamp, et al.), U.S. Pat. No. 8,435,243, (White et al.) and U.S. Pat. No. 8,679,124, (Lechot et al.), there are similar concerns as mentioned by Sidebotham et al. above. For example, the importance of precise dimensions and the labor-intensive making of a conventional reamer, instead of solving the dulling problem of the reamer. Their solutions were creating a plurality of the cutting surfaces is created by pressing or punching through a ribbon-like shim of metal, typically having a 0.2-0.5 mm thickness. Since the metal shim is relatively thin (compared to the 1-1.5 mm thickness of a prior-art acetabular reamer cup), the plurality of cutting surfaces may well be "sharp enough" at its edge for a single use purpose already, once formed and also bent for assembling. Such shim has overmolded with a spherical plastic substrate using the plastic molding process or coupled with other spherical frame or the center connector made by other materials to create a disposable reamer. Such cutting surface made by thin shim and combination with plastic substrate still did not solve the problem of sharpness of the cutting surface. In other aspect, thinner metal sheet can be used as in making regular reamer does not mean it can be a solution for a disposable one regarding to its strength and sharpness of the cutting surface. In addition, making each individual spherical radius of the reamer must be equipped with a series of corresponding tooling(s) for each part. The total tooling cost would add on to the final cost of reamer per use. If there is no large enough quantity required, the cost per use of the disposable reamer might not be less than one of reusable reamer.

The subject matter of a prior U.S. Pat. No. 8,771,275 (Xie et al.) of the present inventors is hereby incorporated into the present application. In U.S. Pat. No. 8,771,275, a new principle of reaming a hemispherical surface referring to the idea of "a ball in the cup" had been proposed. Specifically, a circular cutting element is offset by a specific distance between a center or a cutting plane of cutting element and the spherical center of the sphere and by a specific angle between a cutting axis of the cutting element and a longitudinal axis. When it rotates around a longitudinal axis, it generates a partial spherical surface. Simultaneously, the circular cutting element is able to self-turn around its own cutting axis freely. According the geometric rules, the device with such design can create a perfect hemisphere through one axial reaming. But it also exposes several disadvantages or has potential room of improvements:

- A self-turning of the circular cutting element in the structure would require a complicate mechanical support of the reamer, which would limit numbers types of reamer design.
- The cutting edge of the circular cutting element used has contacted the surface in pin-point manner and can only scratch the surface instead a peeling off like one in cheese grater. So the cutting efficiency of reaming is deducted and is lower than one of the cheese grater.
- To be a tradeoff, the complicate mechanical structure of the reamer required would cause that some functions of the reamer is undoable or less reliable as well as too expansive.

According to such a new cutting principle of the present invention, the circular cutting element provides more freedom on designing a better circular cutting element, in term of improving the cutting performance of the reamer. For example, better sharpness, an ideal way to cut the surface, and reducing its processing steps and final cost are desirable.

SUMMARY OF THE INVENTION

In certain implementations of the present invention, there are several selections in designing and manufacturing edge configurations on cutting member of the cutting elements, regarding to the variations including: a shape, relative position toward the support member, a contact angle toward the spherical surface to be cut, a sharpen-able cutting edge, a special feature or format of notches and its distribution along the cutting edge in order to either enhance its cutting behaviors and cutting results of the cutting element or simplify the method of the manufacturing steps and various methods of assembling them together.

In certain implementations of the present invention, there are selections on the types of cutting elements regarding to the configuration and orientation characteristics, such as one defined by either the geometric parameters alone, called the type I cutting element, or one defined by both geometric parameters and positional parameters, called the type II cutting element, or one only defined by edge configuration of cutting member, called the type III cutting element; as well as a corresponding methods for assembling a reamer by each type of the cutting element.

In some implementations of the present invention, there are several selections disclosed in methods for assembling a reamer, such as a holding member-cutting elements assembling method, Self-Assembling method in order to have various types of reamer and One Size Cutting Element for Several Size of Reamers.

In certain implementations of the present invention, there are options of assembling a disposable reamer. Such as cutting elements either, as an exchangeable part, are suitable for a durable holder, or are united with a disposable holder as a single piece of reamer for a single use and discarded together thereafter.

In certain implementations of the present invention, the cutting element and the reamer in the present invention can be made by both conventional materials and processing method at lower cost and high accurate in its dimension.

The foregoing and other objects, features and advantages of the invention will become more apparent from the following detailed description, which proceeds with reference to the accompanying figures.

BRIEF DESCRIPTION OF THE DRAWINGS

FIGS. 5-1 (a)-(c): (a) show typical features and arrangement of the cutting element (having a receiving member) by sheet-metal processing; (b) shows a cutting element in folded shape and ready for assembling; and (c) a reamer with three symmetric cutting members is assembled by fastening a cutting element and a center connector together.

FIGS. 5-2 (a-c): (a) show a top view of a typical features and arrangement of the cutting element (having a link member) by sheet-metal processing; (b) shows a rear view of a cutting element in folded shape and ready for assembling; and (c) a view of the reamer with three symmetric cutting members is self-assembled by fastening all link members of support members together.

DETAILED DESCRIPTION OF PREFERRED EMBODIMENTS

The following description and embodiments, as well as figures are exemplary in nature and are not intended to limit the scope, applicability, or configuration of the invention in any ways. Various alternatives to the described embodiments made with a respect of the function, arrangement of and method of making the cutting elements and a reamer described herein should not depart from the scope of the invention. The following description and embodiments, as well as figures are fully detailed and also within the understandable scope by a skilled person in the art.

Figure 1:
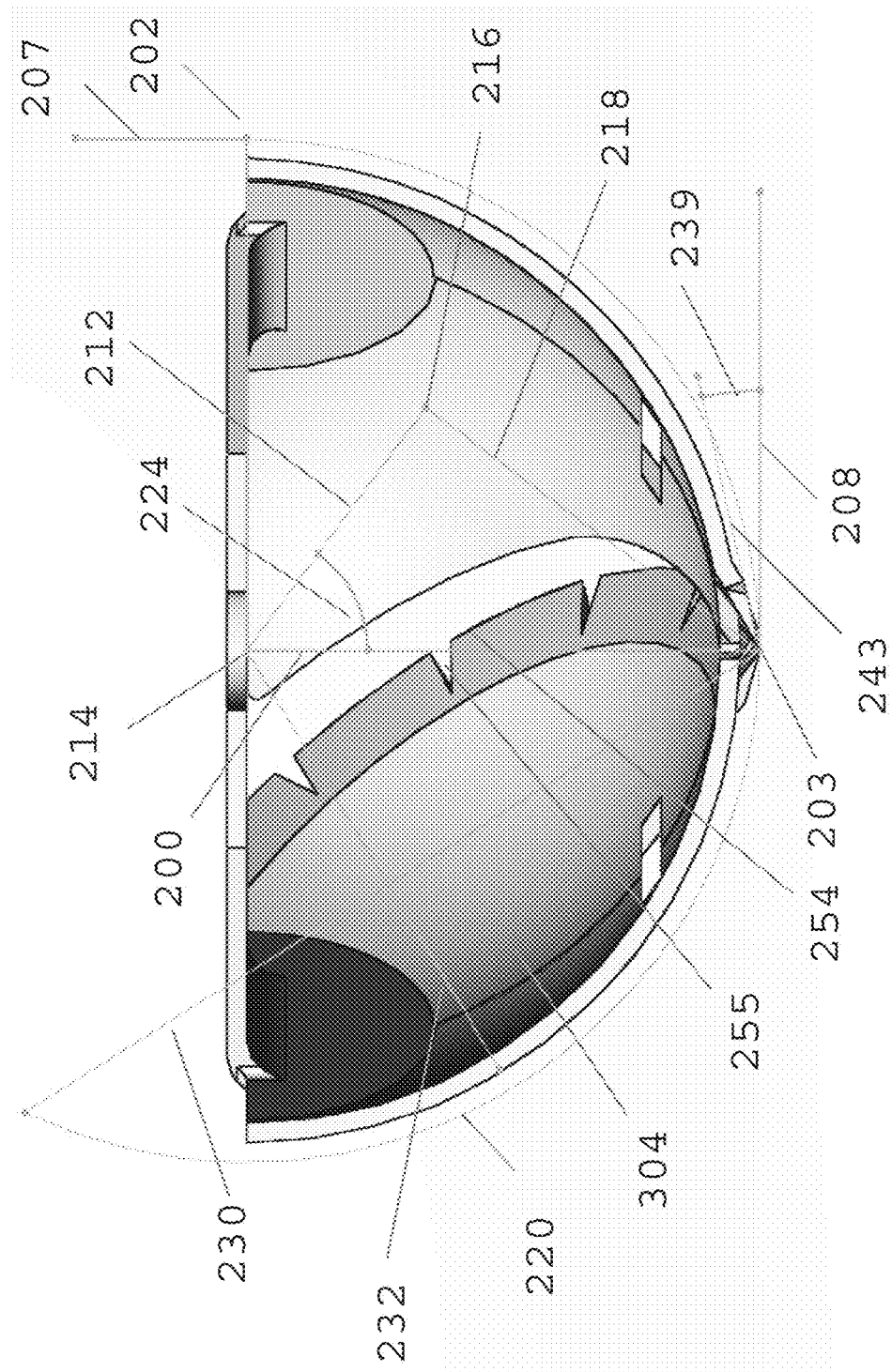
FIG. 1 shows the major geometric and positional parameters of a typical cutting element in the present invention.

Referring to FIG. 1, a typical profile or a surface 220 of a hemispherical cavity can be stacked by multiple latitude circles with a decreased diameter along the longitudinal axis 200 from the equator 202 to the pole 203, so a tangent line of the curvature surface transits from the vertical one 207 to horizontal one 208. Such characteristic predestines the cutting edges of the cutting ware would perform quite differently from region to region, in term of the cutting efficiency. For instance, at uniform rotation speed, there is always over-cutting in the equator zone and a less efficient cutting in the polar zone due to the linear cutting speed to be varied along the longitudinal axis. However, varying the features of the cutting edge at each region against the surface 220 to be cut might reduce such the effect.

Further, more leveraging obtained from external primary forces applied, more cutting efficiency of the tool would have, if key features of the cutting edge can conduct those forces in a proper direction of cutting. Similar to all machining system, two external primary forces are applied on processing the part through rotating the cutting tool: an axial force (a vertical force) is applied by the operator, who pushes the tool down against the surface along the longitudinal axis, and a torsional force (a horizontal, tangent force) comes from the rotating power.

Also, comparable to all machining system, criteria of evaluating any cutting ware and optimizing its cutting efficiency of converting the force applied mostly concerns from following aspects: 1) Improving the sharpness/hardness of the cutting edge against the subject, in term of a proper materials used, a feasibility to sharp them and a availability of processing method; or 2) orientating a proper contact angle between two parties at the cutting spot; or 3) Increasing the total contact area of the cutting edges against the surface to be cut. All of these concerns would be addressed in the present invention and applicable on designing a cutting member and a cutting element hereinafter.

The cutting principle used in the present invention is coincident with the new principle called, "a ball in a cup" mentioned. A circumference edge of a cup with any sizes (being less than the diameter of the ball) can intimately contact with any portions of the spherical surface of the ball by its edge. If the contacting circumference edge can be imagined as a circumference cutting edge, called a Cutting Member hereinafter, which has a continual, cutting edge (including unlimited cutting points exposed to the surface to be cut) which offsets from and rotates around the longitudinal axis of the sphere, it can cut a perfect spherical surface.

In addition, one reamer can equip several circumference cutting members. So, total contact area covered by the cutting members would lead a relatively high cutting efficiency per rotation of the reamer.

All cutting elements discussed in followings can be made by conventional materials routinely used in medical field, such as metal, ceramic and plastics and available methods selected from a group of methods: punching from the metal sheet, the powder metallurgy, precision casting, insert molding injection and others, respectively. Also the cutting element is assembled by the methods selected from a group corresponding to its making method: such as metal welding, ultrasound heating and others. Due to reasons above, the concerns of hardness, sharpness and thickness of the cutting member is no longer a problem in the present invention.

Figure 2:
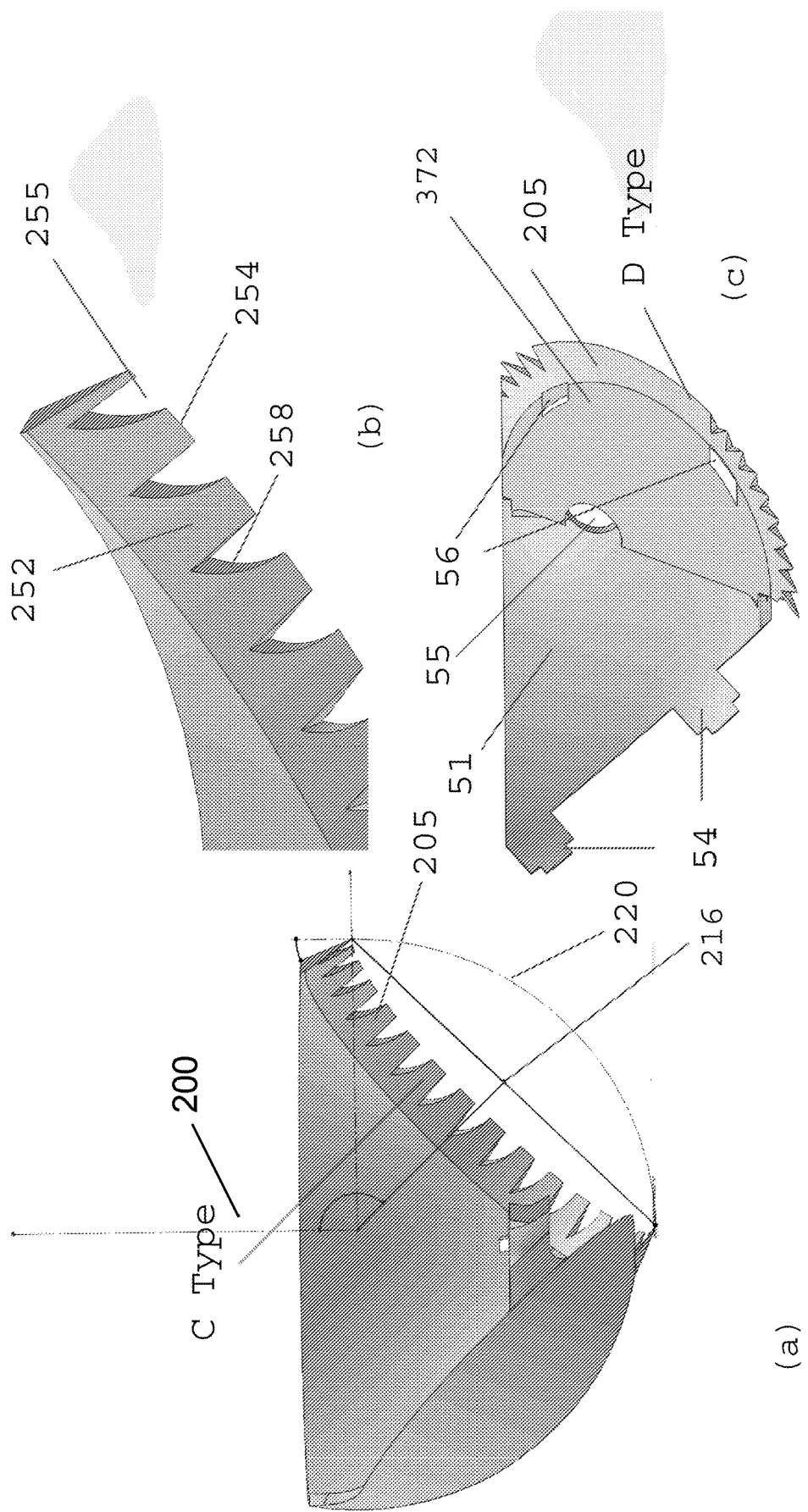
FIGS. 2 (a)-(c) show the major geometric parameters of a typical cutting element in the present invention and various cutting member of the cutting elements arranged. Specifically, (a) shows a C type cutting member; (b) shows edge configuration of the cutting member; and (c) shows a D type cutting member on the support member.

Edge Configuration of the Cutting Member:

In general, the term "a cutting edge" used in the present application is defined as a "coarse" edge, because it is made by regular stamping/punching, which forms a right angle edge on its edge or without additional treatments (e.g. sharpening) applied. Referring to FIG. 2, the cutting member 205 can further comprises a primary bevel on either side, like the one on a chisel, or on both sides of its backbone, like the ones on a regular knife, to form a primary cutting edge 254 on the tip of the cutting member, or called an end cutting edge of cutting member. The primary cutting edge 254 can be formed by conventional method or be easily sharpened from its outer surface during a conventional processing or maintenance step, even though during time out of the operation because the continual circumference edge is fully exposed. So, the primary cutting edge 254 formed is sharpable and has a very thin and sharp edge after sharpening, similar to a knife and can be durable for multiple usages and capable of dealing with any types of bone format or quality if made by proper materials. However, the sharpness of such cutting edge in the present invention is no longer a problem of causing unexpected shorter functioning life as the reamers in the prior art.

Referring also to FIG. 2, a primary cutting edge 254 with a primary bevel can further comprise a plurality of notch 255, as an additional feature of the cutting edges. The desired numbers and types of the notches can prolong the total cutting edge area exposed to the surface 220. Various selections of notches formed on the primary cutting edge 254 include a symmetrical or asymmetrical V-shape 258, a round shape rake notch or others selected, as well as an option of how the notches to be distributed along the primary cutting edge 254. The distribution of the notches along the cutting edge depends upon requirement of the cutting efficiency of the cutting edge in particular region of the sphere 220. Of course, the shorter break interval between adjacent notches, better cutting efficiency of the cutting element presented. As well known in other cutting wares, the primary cutting edge 254 with notches 255 appears a coarse cutting behaviors and higher cutting efficiency than the one without notches. Referring to FIG. 2 (*b*), such cutting effect can be further enhanced by adding another primary bevel on the side wall or edge of each notch 255 for creating a side cutting edge, called a secondary cutting edge 258. A similar example is the serrated edge on a knife. Consequently, such side cutting edge 258 added provides a different cutting feature to each cutting edge and is more powerful on cutting off the texture on the target from different angles, such as, a bone, soft tissue, particularly on the area or spot, which has a weak cutting effect by the primary cutting edge (at the polar zone). The novel cutting edge disclosed hereinafter can convert the pushing as well as the torsional force differently as one of the primary cutting edge in order to further improve the cutting efficiency.

The primary bevel angle on both the primary cutting edge 254 and the side cutting edge 258 of the notch 255 are selectable and depends upon its location on the circumference and a preference of the cutting efficiency desired. Such a detailed feature of notch can be achievable through conventional processing methods and affords an additional option on designing the cutting edge, with respect to better cutting behaviors, strength of the cutting member and the feasibility of manufacturing them.

Referring to FIG. 2, since the cutting axis of the cutting element positioned possesses a desired arm angle 224 toward the longitudinal axis 200, a cutting fashion of the primary cutting edge 254 acting at each cutting point of the surface 220 would be physically varied from the equator 202 to the pole 203 of the sphere 220. Typically, along with both the curvature variations of both a spherical surface 220 and the radial line at each cutting point of the cutting member, their cutting behaviors can be classified in different cutting modes regarding to its manner of contacting the surface 220 (from a 3-D view): an Straight Cutting Mode and a Lateral Cutting Mode, respectively. The Straight Cutting Mode is defined as the primary cutting edge 254 frontally, straightly faces the surface to be cut (the radial line of the cutting point is parallel, co-plane with or at the same level of the corresponding latitude circle plane of the surface 220), similar to a manner of that a plane cutting edge faces wood surface to be cut. The Lateral Cutting Mode is defined as the primary cutting edge 254 laterally faces the surface to be cut (the radial line of the cutting point is offset from the level plane of the corresponding latitude circle). For instance, at the area near the polar zone and the equator, the primary cutting edge reams the surface 220 by the typical Lateral Cutting Mode. At the area near the intersected point on which the radial line of the cutting point and plane of the corresponding latitude circle overlap together, the primary cutting edge 254 reams the surface 220 in the Straight Cutting Mode, a peeling off mode. In the sections between the two regions, reaming behaviors of the primary cutting edge 254 has a mixed fashion of the two typical cutting modes in various ratios. Obviously, the Straight Cutting Mode more efficiently executes the torsional force on the surface 220, but less uses the pushing force. The Lateral Cutting Mode can only partially execute both the pushing and the torsional forces applied on its cutting.

Referring to FIG. 2(c), side edges of the notches located at the upper portion (near the equator zone) of the spherical surface 220 can face the direction of 2 to 3 o'clock and opposite side edge of the notches located at the lower portion (near the polar zone) faces the direction of 7 to 8 o'clock, respectively. Such side edges in these two areas would more efficiently conduct and utilize pushing forces applied than the primary cutting edge does, due to the manner of how the side edge meets the surface 220. Thus, the notch 255 from location to location can have different demands of cutting and can be managed through varying the type and the distribution of the notches accordingly. From this aspect, the pushing force can particularly enhance the cutting results of the notches at specific area to be cut, e.g. the polar area. Logically, the more spherical area to be cut in the Lateral Cutting Mode by the primary cutting edge 254, the more notches 255 needed. The types of notches formed and their arrangement is feasible through conventional processing steps, which bring another advantage for modifying the cutting element's behavior in a reamer design. Thus, the "decent" cutting edge having all features described above defines the term "cutting member" hereinafter.

Figure 3:
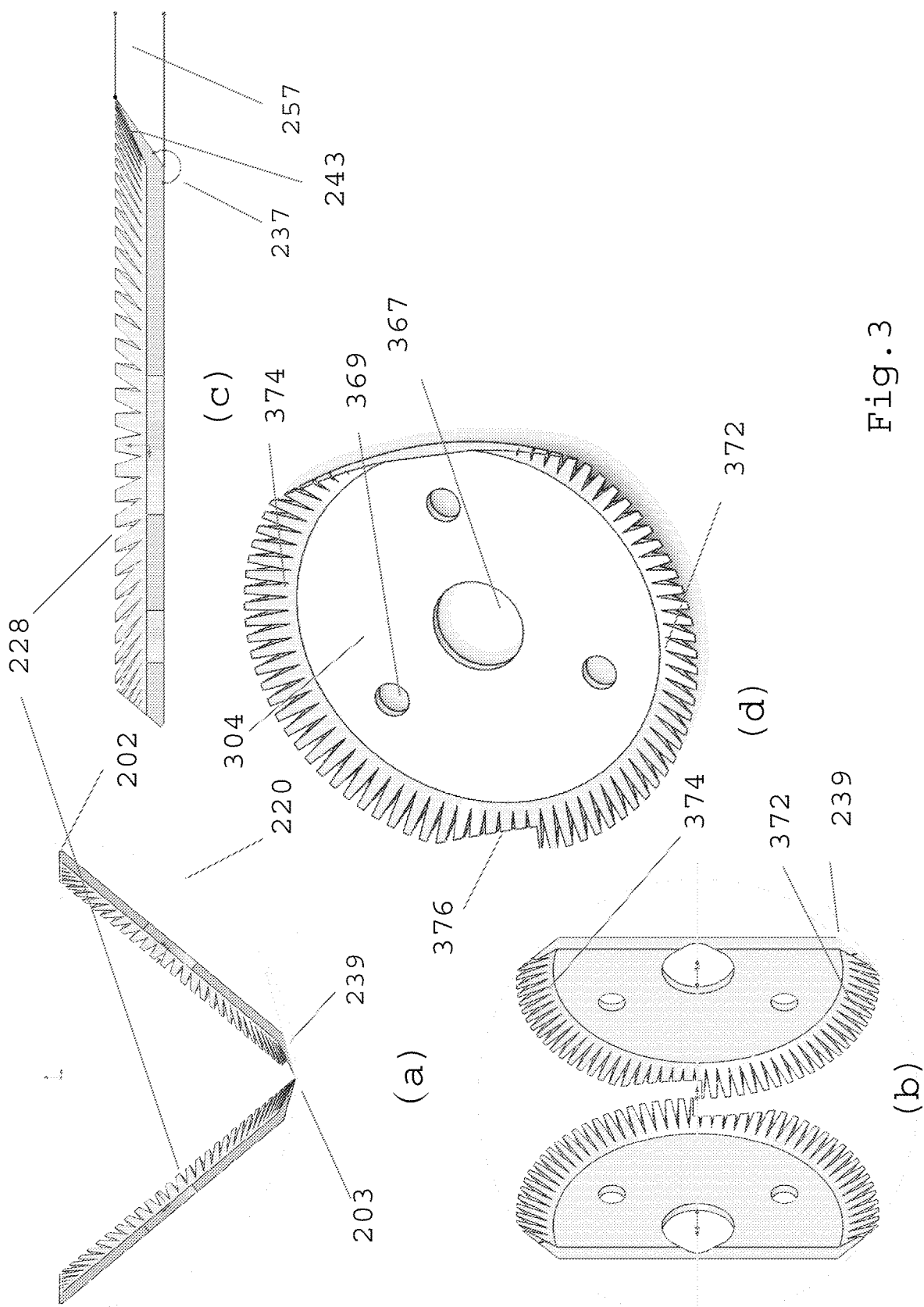
FIGS. 3 (a)-(d) show typical features and arrangement of the cutting element.

Configuration of the Cutting Element:

Referring to FIG. 1 to FIG. 3, at each contact point between a cutting member 205 and spherical surface 220, there is a contact angle β, 239 of the cutting member, defined between a backbone or outer surface 243 of the cutting member 205 and a tangent line 208 of the contact point on the spherical surface 220. Referring to FIG. 1, the cutting member 205 is inwardly extended from the support member 304 and bent by a bending angle 237 towards the cutting axis 212 to form a desired contact angle 239 to the surface to be cut and a bending height 257 of the circumference edge. In other embodiments, the cutting members are inwardly arched by a desired arch (also forming a bending angle to the backbone of the cutting member) towards the cutting axis to create a desired contact angle and a height of the circumference edge. Such the bending height 257 and the bending angle 237 here determine a virtual cutting radius 212, a virtual cutting plane 228 and the contact angle 239 of the cutting member, regardless of the bending fashion listed above. Similar as one in other cutting wares, rationalizing the contact angle β, 239 would optimize a cutting behavior, efficiency of the cutting ware and a quality of the surface 220. In regarding the types of cutting members mentioned above, a desired angle bent to the surface to be cut 220 at any region/section of the cutting edges are manageable during its manufacturing. Selectable contact angle of the cutting member and varying it from region to region can be one of the advantages of the present invention for designing the cutting elements. Smaller contact angle 239 formed, the more aggressive cutting behavior of the cutting edges does. It brings a primary factor for modifying/varying a cutting member behavior in the reamer design of the present invention. The contact angle 239 of each cutting element designed also correlates with the radius of the spherical surface to be cut and a cutting efficiency and behaviors needed in each region of the surface. The contact angle optimized should be a range between 5 and 30 degrees from case to case.

In general, the term "a cutting element" defined in the present application comprises a cutting member(s) extended from a corresponding support member and is ready for assembling a reamer.

Referring to FIG. 1, according to the above mentioned "a ball in a cup" principle, a spherical diameter, y, and dimension or area of the spherical surface 220 to be reamed by a reamer can be basically determined by the geometrical parameters and the positional parameters of a circumferential cutting element, respectively, which defines as:

Positional parameters includes an offset distance, called an Arm Length d, 212 defines a distance between the spherical center 214 and the circular center 216 of the cutting member; and an offset angle, called an Arm Angle α, 224, defines a angle between the longitude axis 200 and the cutting axis 212 of the cutting member, while the cutting axis 212 is defined by a line between the spherical center 214 and the circular center 216 or cutting plane of the cutting member; and Dimensional Parameters: The Radius of the Cutting Member.

Further, the geometrical parameters can also include: a circular center, a virtual cutting axis, a virtual cutting radius and a virtual cutting plane 230 of cutting member 205. The positional parameters mostly consider a position of cutting member relative to the spherical center 214 and the longitudinal axis 200. The edge configuration of the cutting member 205 can include a contact angle 239 or a bending angle formed, a bevel angle, a notch and its distribution thereof. All parameters together are necessary factors for defining a cutting element as well as a spherical radius of reamer. According to the criteria above, the types of cutting element can be classified in followings:

Type I Cutting Element comprises a cutting member 205 extended from a support member 304. The cutting member 205 has its edge configuration and is further defined by geometrical parameters, while it extended from or imbedded into the support member 304, but its positional parameters toward the longitudinal axis 200 and spherical center 214 would be determined by a corresponding orientation of a mounting member or center connector of the reamer.

Type II Cutting Element comprises cutting member(s) extended from or imbedded with a support member 304. The cutting member(s) 205 has its edge configuration and orientation with respect to the link mechanism on the same support member and is further defined by both geometrical and positional parameters while the reamer assembled. The cutting elements formed are ready to be either held by the holding member, center connector of the reamer or be self-assembled together by the link mechanism.

Type III Cutting Element comprises a cutting member only having own edge configuration and being ready to be imbedded into and be shaped by a pocket or envelop of the support member or the reamer frame or the center connector. A shape and orientation of the pocket or envelop determines both the geometrical and positional parameters of cutting member of the Type III Cutting Element.

Further, referring to FIG. 3, as a case of Type I cutting element, the support member 304 of the cutting element comprises a frontal/leading fringe 372, a rear/trailing fringe 374. A configuration of the support member 304 is selected from the groups of a dish-like 355, an annulus, a cylinder, a partial circumferential edge, a ribbon and others or their combinations. A location and an orientation of the cutting member built on the support member depend upon the function and the type of the cutting element, as well as a manner to be assembled (e.g. reusable or disposable). Even through various shapes of the support member 304 in Type I cutting element, its function can be same and include that the cutting member 205 is extended from support member 304 (here also called a base portion) to form a cutting radius 218, cutting plane 230, contact angle 239 and provides an interface 367 to be ready for coupling with a mounting site of the frame or the center connector of the reamer.

Structurally, the circumferential edges of the cutting member can be further classified into two half regions: a frontal/leading region, starting from 6 o'clock to 12 noon in the counterclockwise rotation, and a rear/trailing region, starting from 12 noon to 6 o'clock in the counterclockwise rotation, with respect to the arrangement along the fringe of the circumference. There are two types of the cutting member located on each region:

Referring to FIG. 2(a) and FIG. 8(a), A C-type cutting member 234 and 85 refers a circumferential edge counterclockwise from 180 or more to 0 degree, if the 0 degree points at 6 clock position or polar point, and forms a concave cutting edge 234, (like an concave edge of a letter C) along backwardly, excessively arched guide line behind its center line. No matter on which region it is located and what type of edge configuration has, the primary cutting edge always starts from polar point and can be in either a full half circle or a partial half circle.

Referring to FIG. 2(c) and FIG. 8(b), a D-type 205 and 83 of the cutting member refers a circumferential edge clockwise from 180 or more to 0 degree, if the 0 degree points at 6 clock position or polar point 203, and forms a convex cutting edge 205, (like an convex edge of a letter D) along excessively, forward arched guide line with a respect to its center line.

Figure 8:
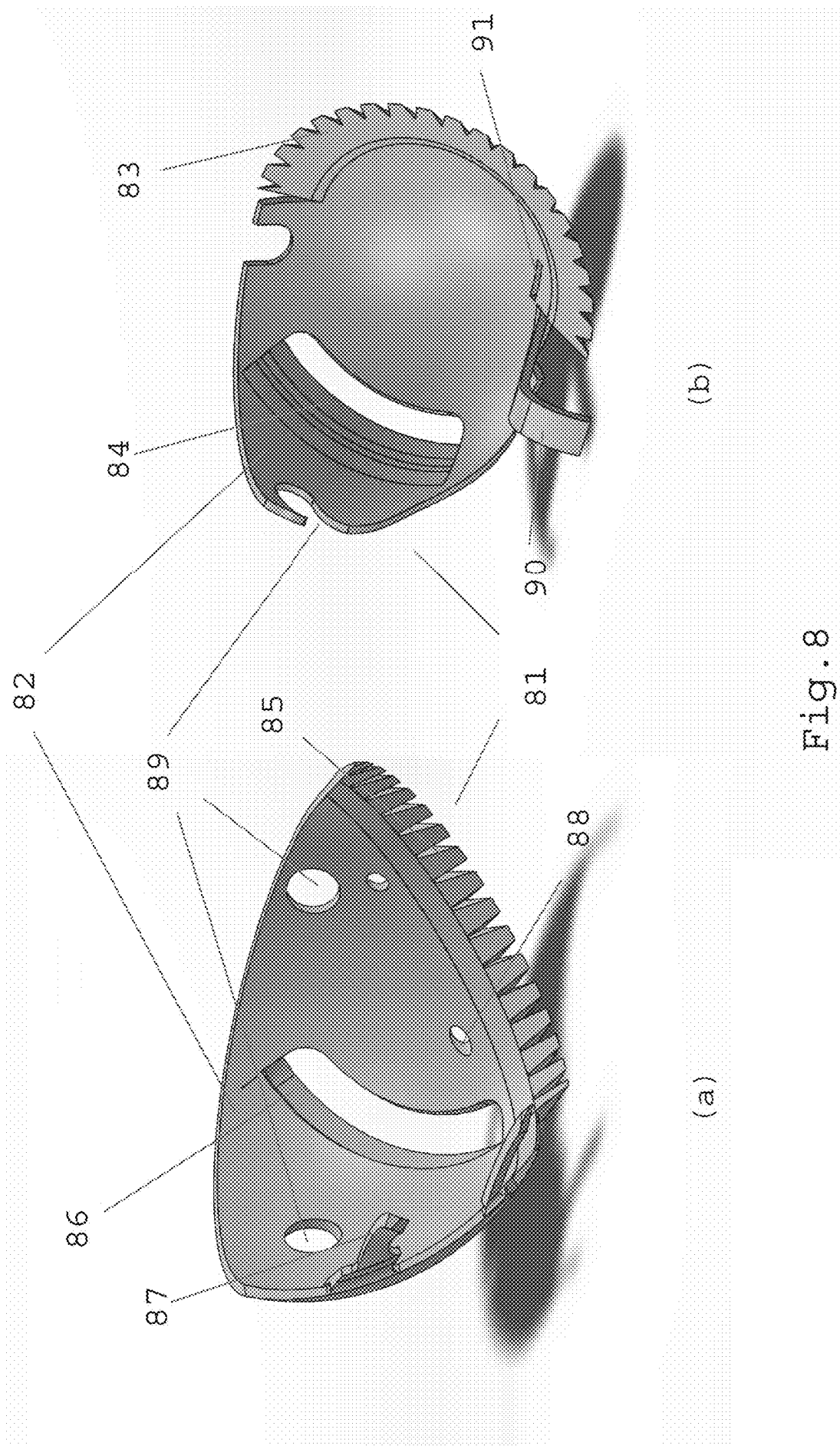
FIG. 8 shows features of a Type II cutting element having a primary and secondary cutting member built on the support member and a link mechanism for methods of self-assembled.

Referring to FIG. 8, in other case, a support member 82 comprises two cutting members on the support member. A primary cutting member located at the leading fringe of the support member 82, is able to cut at least area from the equator to the pole, even though its circumference edge of cutting might be less than a half circle, and can have a shape of either a D-type 83 or a C-type 85 cutting edge, as shown in FIG. 8(a) and FIG. 8(b), respectively. A secondary cutting member 86, as shown in FIG. 8, locates at somewhere between the leading and the trailing fringe of the support member 82 and usually combines with either type of the primary cutting edge 83 or 85 on the same support member 82. Two cutting members have an identical cutting radius and a cutting plane and comply with the geometric rule. The secondary cutting member is able to only cut area except the equator and the pole point of the hemispherical surface, and can only have a C-type cutting edge.

Figures 1, 5:
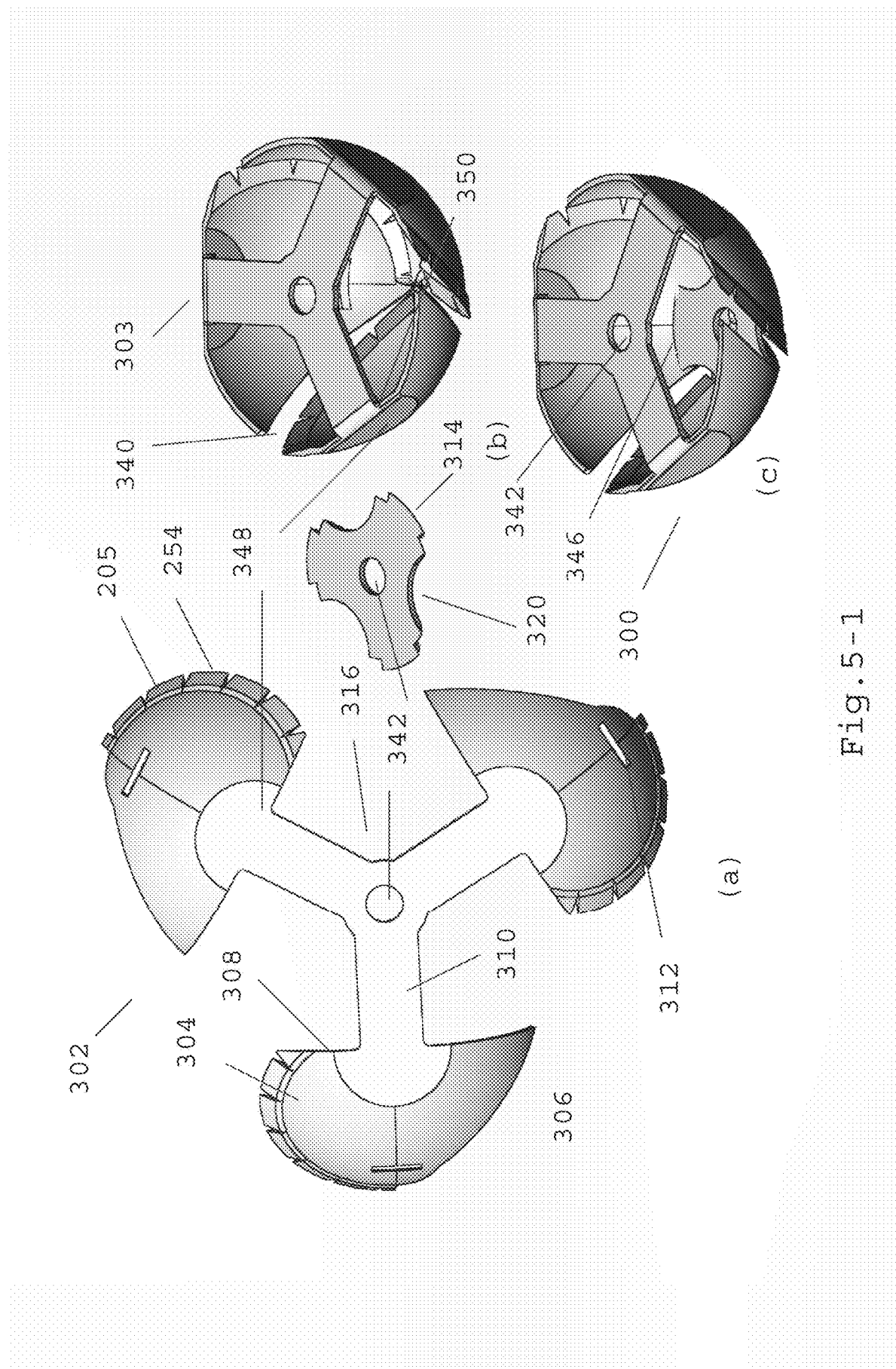
Figures 2, 5:
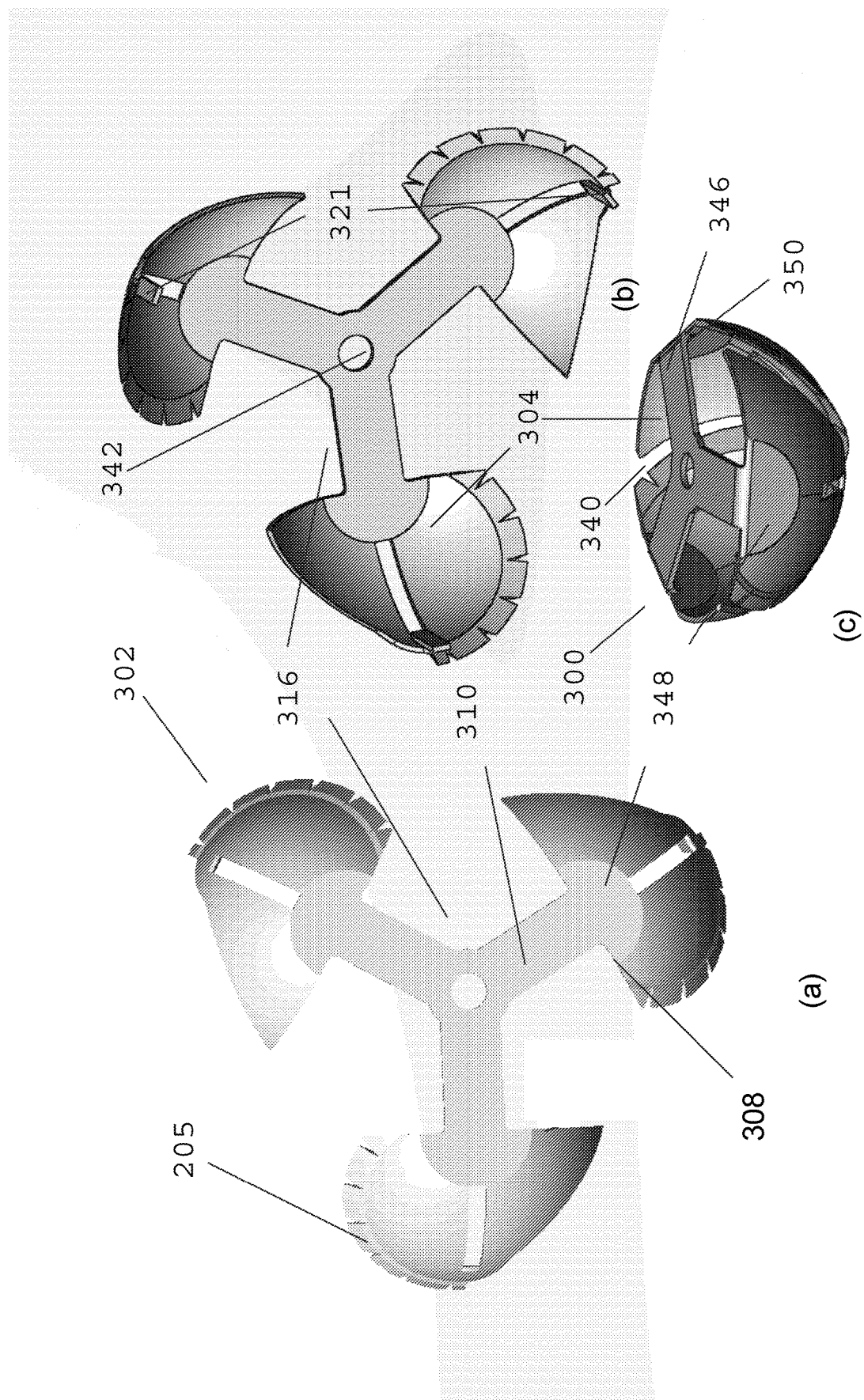
Figure 9:
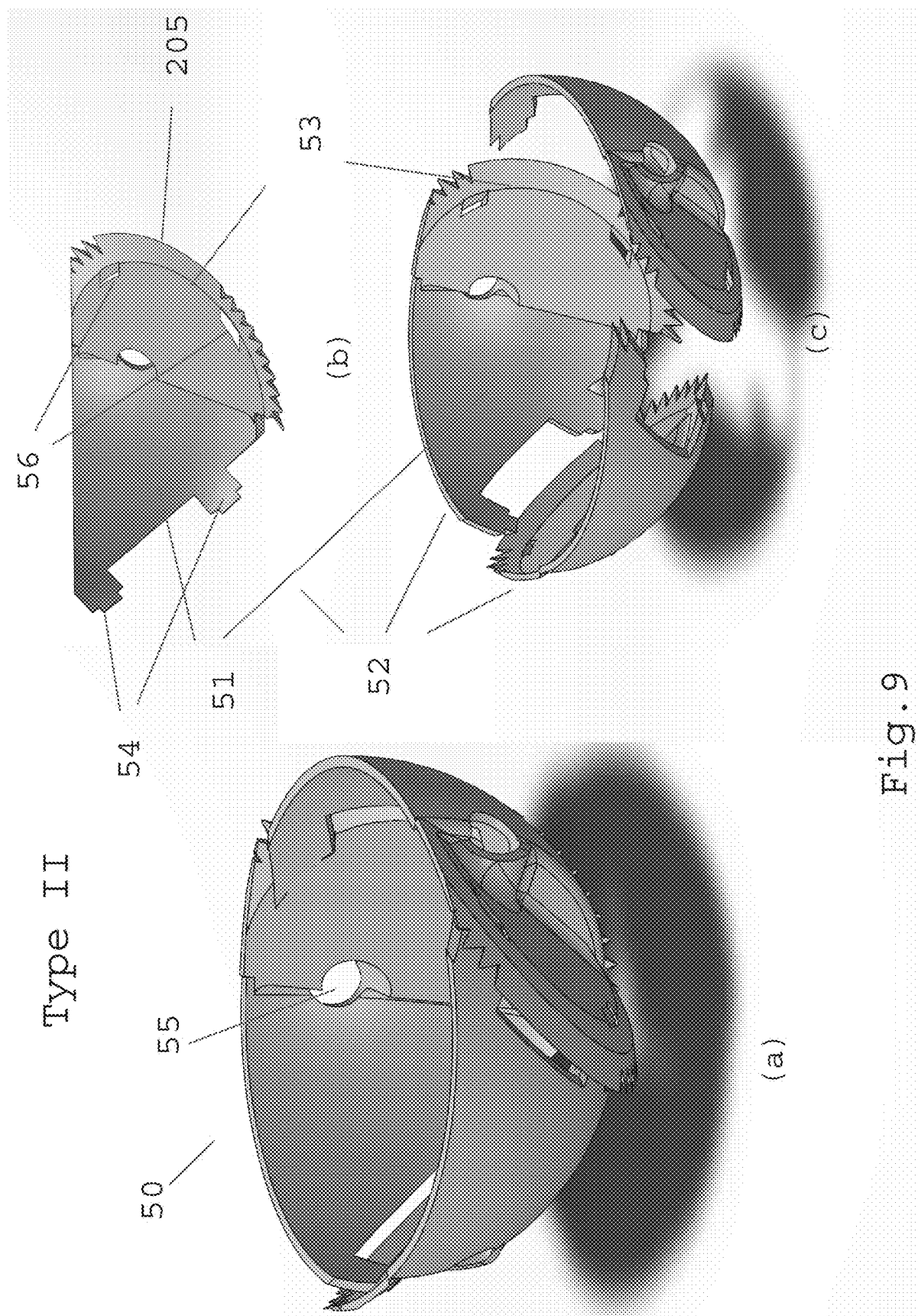
FIG. 9 shows a typical Type II cutting element and a reamer self-assembled.

A function of the support member in Type II cutting element can include: 1) the cutting member(s) is extended from or imbedded with the support member to form and position it in proper format and preset orientation (two parameters); 2) either a connecting member 644 is able to directly link two sequential support members 651 together and bent to specific direction, so the corresponding cutting members 660 orientated toward the longitudinal axis and the spherical center, as shown in FIG. 5, 6(c), or one as shown in FIG. 9, the connecting member 54 on the first cutting element unites with the second receiving member 56 on the sequential cutting element together, the first receiving member 55 of support member 51 further joins the center connector, which is able to couple with the driving shaft.

The support member in Type III cutting element is optional. Its function can be as either a linking ribbon that connects all cutting members/edges 604 together or a positioner for conveniently locating cutting members during insert molding, referring to FIG. 4.

According to the cutting principle of the present invention, the Type I and II cutting elements are also suitable for assembling a reamer with different size, by same cutting element. The method is called "One Size Cutting Element for Assembling Several Size of Reamers" method, ("one for several" in short hereinafter), if corresponding parameters, e.g. the arm angle, arm length, cutting diameter of the cutting edge and identical cutting planes, all satisfy the principle, referring to FIG. 10.

Configuration of and Methods of Assembling a Reamer:

In general, a reamer assembled by type I of cutting elements discussed above can be in following formats: 1) a reamer has disposable cutting elements coupled with a mounting sites of a durable frame or a center connector by a locking mechanism, discarded the cutting elements when it got dull; 2) a reamer (either reusable or disposable one) has cutting elements assembled with a mounting site of a frame or a center connector; or fused together at a preset arm angle and arm length and discarded them together when reamer got dull.

In the first case, the reamer can comprise of at least one main frame or a center connector having a plurality of symmetrical arranged mounting sites, and/or corresponding cutting elements, as well as other similar accessory components, if necessary. So each cutting element/member can be releasablely mounted or imbedded on the mounting site of the main frame or the center connector.

According to the principle, each cutting member with a given cutting diameter is suitable for cutting various sizes or portion of the spherical surface, if it is positioned at a corresponding arm length and/or arm angle being different from ones in the other reamer. Consequently, the geometric rules would lead to two applicable formats for forming a specific spherical reamer: 1) If a same size cutting member is positioned by holding members or self-assembled at a different arm length of cutting, the reamers built has different spherical radius. 2) If a reamer is equipped with identical cutting members having a specific diameter and is able to continually vary at least the arm length of the cutting element, the reamer becomes an expandable reamer.

More particularly, "One for Several" methods can form several sizes of reamer, if the conditions are satisfied. According to the geometric rule, there are ways to assembly such a reamer with various spherical radius from same cutting element:

A fixed angle method: all the cutting elements having identical geometric parameters assembled can have a same arm angle, but a different arm length for assembling a different spherical radius of reamer. For example, referring to FIG. 10(a), if the cutting elements 520 having a specific cutting diameter 521 are assembled together and present a fixed arm angle 522 and a first arm length 524, the reamer built has a first cutting radius 561; and if it presents a same arm angle 522, but a second arm length 526, the reamer built can cut another size 562 of the spherical surface. In this case, all cutting elements have same cutting radius and are always symmetrically arranged, ream identical area of the surface to be cut. The parameter variations only change the spherical radius of the reamer.

A varying angle method: if the cutting elements are assembled in a manner by simultaneously and symmetrically varying both the first arm angle 532 to the second one 538 and the first arm length 540 to the second one 534 of the corresponding cutting elements 520, the spherical radius of reamer formed are changed from first one 530 to second one 550. Simultaneously and symmetrically changing both the parameters (angle and length) is equivalent to swinging the cutting plane around the polar point 542 of the sphere. A swinging angle is defined as an angle between the longitudinal axis and the cutting plane of the cutting member. Referring to FIG. 10(b), according to geometry rule, the cutting element 520 having a specific cutting diameter can cut a first spherical surface 530 at the first swinging angle of the cutting plane; and cut a second (enlarged) spherical surface 550 with another, enlarged, swinging angle of the cutting plane around the polar point, as a pivot 542, referring to FIG. 10(b). In this case, all cutting members have same cutting radius, ream identical area of the surface to be cut. It means event though both the arm angle and length of all cutting members have changed from previous one, they are still in symmetrical layout, at which all cutting elements have a same arm angle, so the cutting area are same. The parameter variations only change the spherical radius of the reamer.

A overlapping method: referring FIGS. 1 and 7(c), each cutting member having a same radius is orientated at own unique position toward the longitudinal axis and the spherical center of the reamer and cuts different, but partially overlapped latitude of the surface to be cut. In order to vary the spherical radius of the reamer, the arm angle 224 of each cutting member is different from others, no matter the spherical radius. In a case of enlarging spherical radius, the arm length 212 of all cutting members is simultaneously expanded; but the arm angle 224 or the cutting axis of one cutting member 426 is tilted toward or turned direction of the equator 202, oppositely, the arm angle 224 or the cutting axis of another cutting member 425 is tilted toward or turned to the polar point, so the arm angle for each cutting element is asymmetrically changed and the overlapped cutting area by two cutting member becomes less along with enlarging the spherical radius of reamer. Even though all cutting elements have same cutting radius, each cutting element reams different area of the surface to be cut.

The "One for Several" methods described in the present invention can be fulfilled with the help of a concave mold having a spherical cavity, or the likes, with a desired dimension of a reamer to be assembled. Referring to FIG. 10(c), for example, a connecting member 550 on each support member 552 of the cutting element 554 is connectable with a second receiving member on the sequential support member 553, then the cutting elements are well positioned in term of a desired orientation and position toward the longitudinal axis and the spherical center, respectively, while they sit in the spherical concave mold 556 and all the cutting members intimately contact with the spherical surface 560 of the cavity, then all the cutting elements are united together and their status are fastened by properly mechanical processing (welding or similar) the link mechanisms together, such as Tenon-Mortise joints or any equivalent features. All cutting elements assembled by methods discussed above could be further strengthened by center connector joined with the first receiving member, which is also an interface for coupling with the driving shaft.

Each size of the connecting member 550 on the support member can have allowance on variations of allowing reamer spherical radius about 10 mm in diameters without effecting the dimension accuracy and quality of the cutting results by either the fixed or varying angle method. For instance, a cutting element having a 22 mm cutting radius can assembly a reamer having a spherical diameter from 52 mm 530 to 62 mm 550, (FIG. 10(b)), by the varying angle method. From the point of view of manufacturing, such processing and assembling methods can save significant tooling costs on moldings for making each individual size of the cutting element, particularly for manufacturing a set of reamers having 1 mm increment interval.

Figure 12:
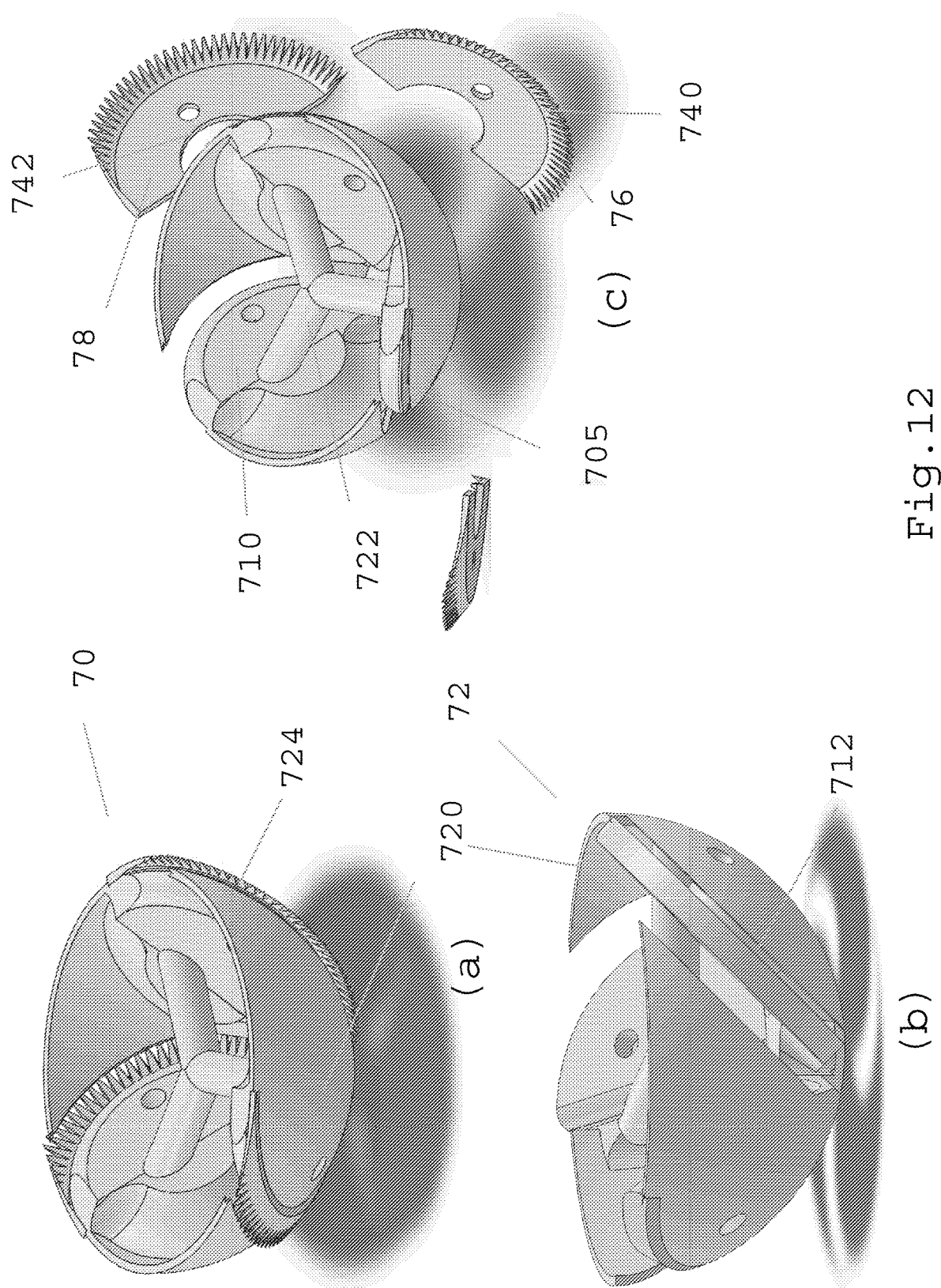
FIGS. 12 (a-c) show a reamer assembled with three cutting elements and a main frame or the center connector as well as its exploded view.

1. Reamer Assembled by the Type I Cutting Element:

In general, a reamer assembled by Type I cutting elements can be: 1) The Type I cutting elements, as a disposable part, couples with a mounting site of a frame or a center connector, by a locking mechanism, discarded when cutting element got dull, referring to FIG. 12. 2) The Type I cutting elements are assembled with mounting sites of a frame or a center connector, (either reusable or disposable one) having a preset arm angle and arm length and discarded them together when it got dull.

Type I cutting element has a structure of cutting members only defined by the geometrical parameters. Its location on the reamer is determined by an orientation and position of the mounting sites on the frame or a center connector. So the method is called "Method of Positioning Cutting Element on the Holding Member(s)". An orientation of the cutting element relies on an orientation of the mounting site or similar component through assembling/coupling. In this case, the cutting elements are either exchangeable part or are integrated with the frame or a center connector as one-piece reamer. Typically, for the disposable reamer, the plastic frame or the center connector having a specific configuration can be assembled with the cutting elements through overmolding, insert molding or ultrasound heating. In addition, the Type I cutting elements can also be assembled by method of "One for several", if a proper frame or the center connector is available, referring to FIG. 10.

2. Assembled by the Type II Cutting Element:

Since the cutting members in the Type II cutting element are defined by both the geometric parameters and the positional parameters or equivalent and are readily for self-assembling a reamer through called Method of "Self-Assembling Cutting Elements" in following manners: 1) the link mechanism, such as a Tenon-Mortise joint, on one support member concentrically couples with the link mechanism of sequential one together to assembling a reamer, while each support member inwardly bent toward the longitudinal axis; 2) or With a help of a center connector, the link mechanism on one support member concentrically couples with the link mechanism of sequential one together to assembling a reamer, 3) or a connecting member links or merges two support members together to be a united cutting element, then a center connector orthogonally couples with the receiving member of the united cutting elements together to be a reamer.

Figure 11:
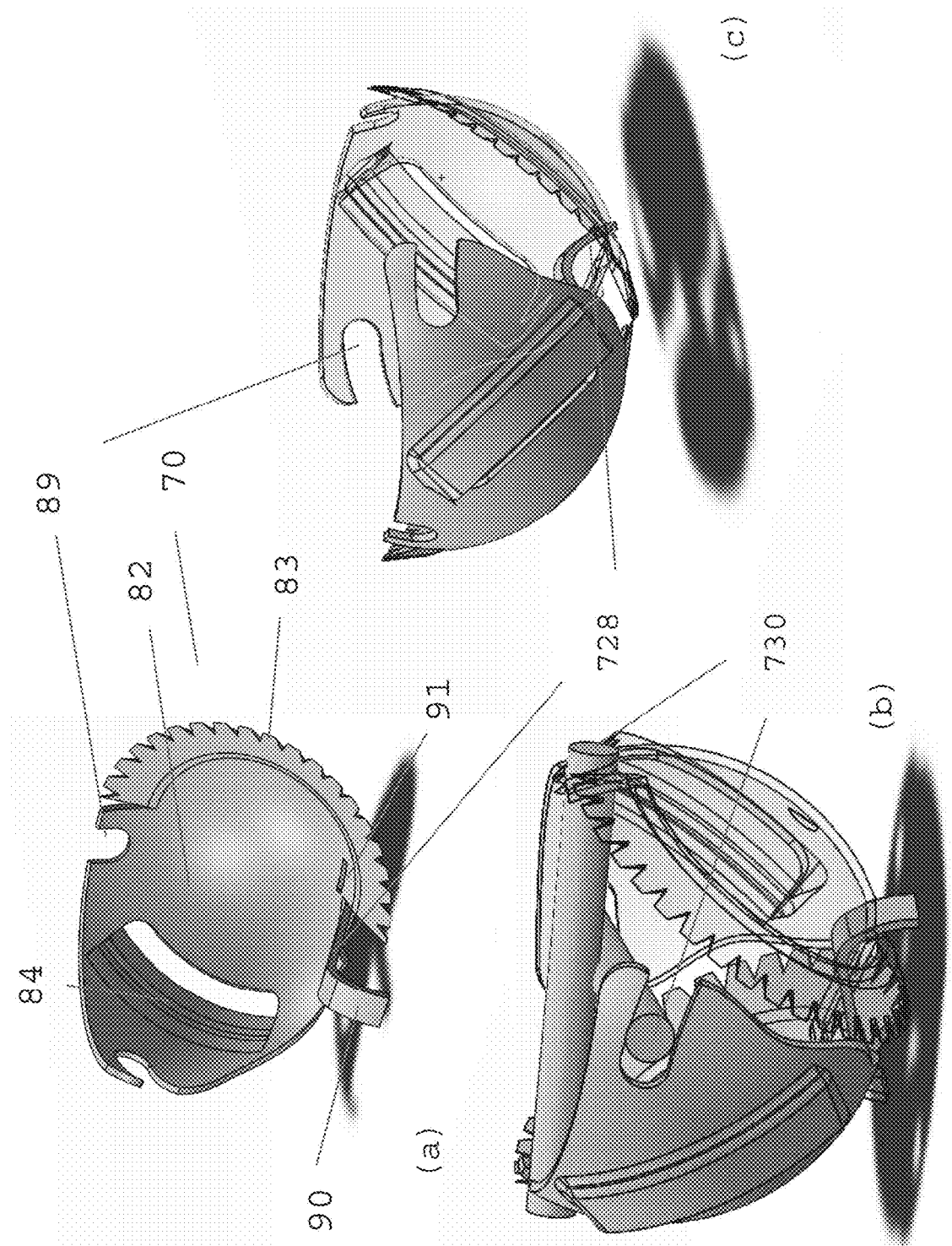
FIGS. 11 (a-c) show details of self-assembling the cutting elements by a varying angle method: (a) shows detail features (the link mechanisms for varying angle) of a type II cutting element; (b) shows the reamer self-assembled in a retracted position; (c) shows the reamer self-assembled in a fully expanded position.

The Self-Assembly method also can be combined with "One for Several" methods, particularly, varying angle method, if the link mechanisms or linkage members are applicable and the orientation of the parts assembled follows the geometric rule above, referring to FIG. 11. The cutting element having specific configuration (if satisfying the identical rule) is able to self-assembly a reamer having different spherical radius according to the varying angle method (swinging the cutting plane of the cutting member by a desired swinging angle around polar point of the sphere). Since the cutting elements are suitable for swinging around the polar point by any desired swinging angle during enlarging the spherical radius of the reamer, for an initial size of reamer formed, the cutting member is able to covers a cutting area about 60% of the total surface range the sphere (its upper edge located above the equator point), in referring to FIG. 11(b). Up to a fully enlarged, a final size of reamer, a cutting area of the cutting member covers at least the hemisphere (its upper edge located at the equator point), referring to FIG. 11(c). So this means a cutting diameter of the cutting member for an initial size of reamer formed is oversized in using the varying angle method.

Figure 13:
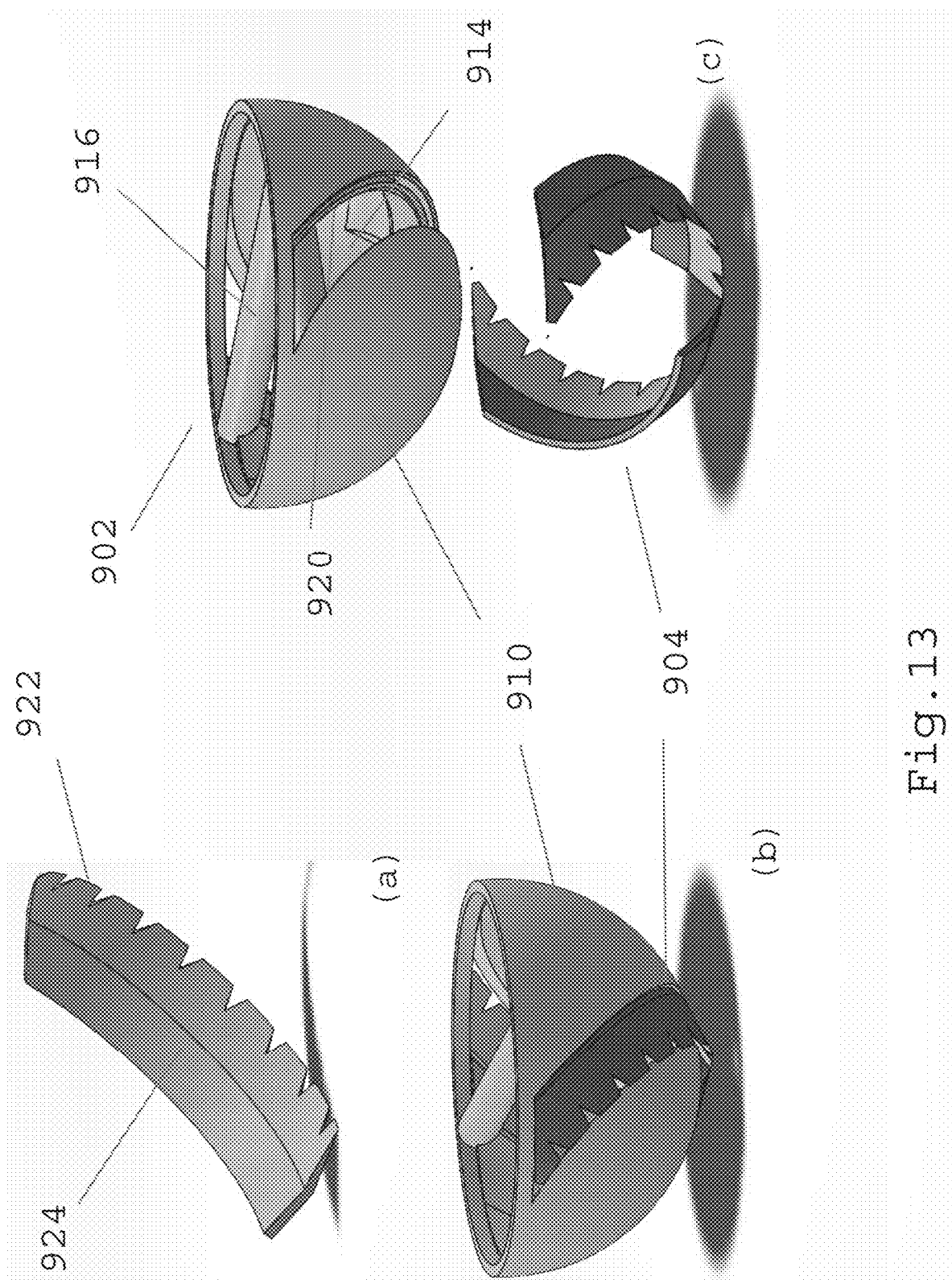
FIGS. 13 (*a-c*) show detail features of Type III cutting element imbedded into envelop of disposable thin shell holder by inserting molding injection. (a) shows a cutting element having a partial circumference edge; (b) shows a side view of a reamer assembled; and (c) shows an exploded view of the reamer.

3. Assembled by the Type III Cutting Element:

Type III cutting element: each cutting element or cutting member, as an insert, is actually imbedded into either a plurality of receiving grooves on a disposable center connector or reamer holder (having a thin reamer shell) as shown in FIG. 13, or into a receiving groove of a disposable support member to becoming a Type II cutting element as described above. For instance, the cutting element has a cutting edge or member in a ribbon shape and is able to be imbedded into a receiving groove of the disposable reamer holder by insert molding method to form a single reamer. An arched receiving groove of the receiving pocket is able to curve the ribbon-shape cutting member to a desired cutting diameter and to position it at the desired arm length and the arm angle. While the cutting member is imbedded with a disposable support member of cutting element, instead of the reamer holder, such a cutting element can be formed as a Type I which only has a specific cutting diameter or a Type II cutting element, if both its cutting diameter and positional parameters is been fixed by the support member.

Figure 4:
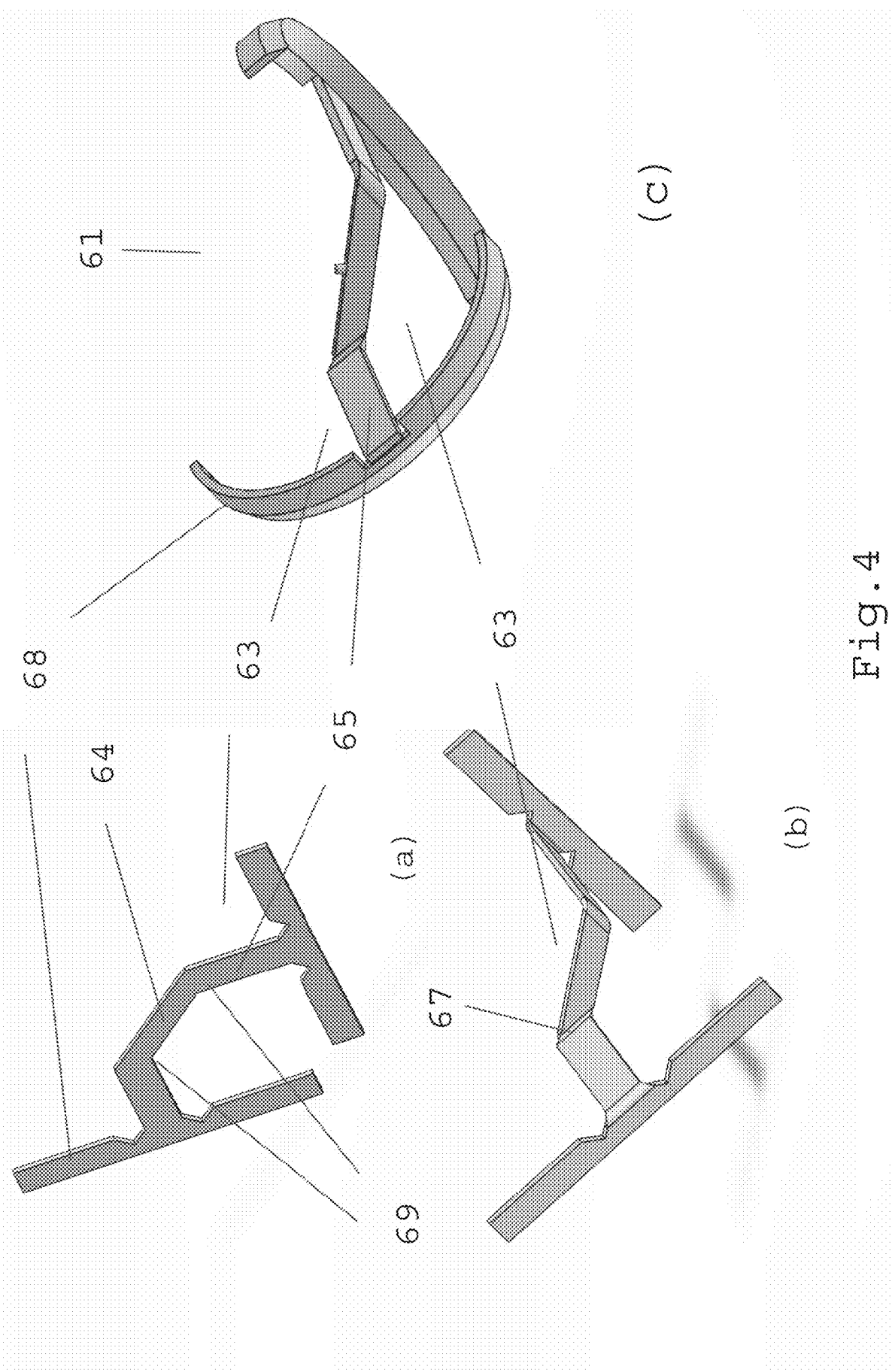
FIGS. 4 (a)-(c) show typical features of Type III cutting element.

In other embodiment of type III cutting element, referring to FIG. 4, the cutting element 61 comprises two cutting members 68 linked by a support ribbon 63. The imbedding fashion of the cutting members is regulated by a shape and positions of the receiving groove of the reamer holder, which includes the cutting radius, the arm angle and arm length of the cutting member.

Embodiment I

Each reamer discussed in the following has a spherical cutting radius, a longitudinal axis and spherical center.

As a first option of a reamer assembled by a Type II cutting elements, Referring to FIG. 1 and FIGS. 5-1 and 5-2, a reamer 300 comprises a cutting element 302 and a center connector 320. As mentioned previously, the cutting element is a Type II Cutting Element because the orientation and geometric format of each cutting member 205 is fixed during sheet-metal processing. It includes a cutting radius, a cutting plane a cutting center and a cutting axis of the cutting member 205. Such the orientation can be defined by preset parameters of the cutting element in sheet-metal format. The preset parameters formed during the sheet-metal processing include a cutting radius 218, orientation or bending angle between a cutting plane 230 and a planar plane of the limb 310, and a proper prolongation of each branched limb 310 from the longitudinal axis, as well as the thin wall radius 232.

Referring to FIG. 5-1(a), the most important features of the cutting element 302 have been done during sheet-metal processing; even it is in 2-dimension format. Before one-piece reamer assembled, the cutting element 302 comprises a connecting member 316 having a center hole and three limbs equally spaced apart from each other. Each limb is horizontally extended from the longitudinal axis to the support member connected at a trailing end of the each limb. Each support member 304 comprises a partial spherical shell thin wall with a radius 232, and at least a link mechanism, such as one link member, or one receiving member 312 located in a lower portion thereof. Three support members 304 have identical configuration and are symmetrically arranged around the longitudinal axis and equally spaced apart from each other by 120 degree angle interval. Each limb 310 has a specific length extended from the center hole to an upper fringe 308 of each support member 304.

For assembling a reamer 300, every support member 304 is concentrically and inwardly bent toward the longitudinal axis by forming a bending angle between a planar plane of the connecting member 316 and the cutting plane of each cutting member and an arm length between the spherical center and the cutting center thereof, while Interfaces 314 of the center connector 320 concentrically couples with the receiving member 312 of each support member 304. Meanwhile each cutting member possesses a position defined by both geometrical and positional parameters and satisfying the geometric rule. The partial spherical thin shell of the support member 304 has a radius less than a spherical radius of the reamer and forms a hemispherical doom, while the reamer 300 assembled. During folding the support member 304, its trailing fringe gets close to the cutting plane 230 of the sequential cutting member, but leaves a 2-4 mm gap 340 between them, as a channel for collecting cutting debris.

Referring to FIG. 5-1(a, b), in general, each extending plane 348, as a transition portion between the support member 304 and the limb 310, initially is co-planar with the one of the limb after sheet metal works and is inwardly bent with the support member together toward the longitudinal axis by a bending angle 350 between the limb 310 and extending plane 348 during folding/assembling step. In this case in FIG. 5-1(b, c), each extending plane 348 is parallel to the longitudinal axis, while is bent. The bending angle 350 between the limb 310 and the extending plane is 90 degree angle. This critical angle bent must be as accurate as possible and fulfilled by help of a spherical concave mold. In other word, at this angle, all portions of the cutting member can intimately contact with surface of the cavity and interfaces 314 of the center connector 320 are able to fully couple with a corresponding receiving members or openings 312 on each support member 304 in order to fasten the all support member 304 in the correct position. Each size of the spherical concave mold used matches the spherical radius of the reamer to be formed. The support members 304 and the center connector 320 are fastened together at each coupling point by mechanical fastening method, such a welding. This key tool can also tests whether or not each folded cutting element 303, as shown in FIG. 5-1(b), well sits into the cavity and all cutting members intimately contact with the surface of the spherical mold.

Referring FIG. 5-1(c), the reamer can concentrically couple with the driving shaft by connecting member 316, while a center pin of the shaft inserts into first and second center holes in both the connecting member 316 and the center connector 320. Both members can differently conduct an axial force (through both members) and a torsional force (through center connector only) through both center holes 342 on the contact surface of connecting member 316 and center connector 320, if the first and second holes have different sizes. From point of view of a skilled person in the art, any detailed features, factors can be added in order to strengthen the structure of the reamer in term of enhancing its reliability and durability.

As an additional example, the cutting element comprises a connecting member with two limbs extended in opposite direction. Each one directly links with a corresponding support member having a cutting member on its leading fringe in a manner described in previous case. Most arrangement of the features is also same as one in previous case, except only having two limbs and a different shape of the partial spherical thin shell. Such the cutting element is initially processed by sheet-metal method for fixing the orientation of the cutting member. Its support member inwardly folded in a manner described in previous case, and then it is ready for assembling. Two cutting elements having an identical configuration can be concentrically and orthogonally stacked on top each other along the longitudinal axis and then all support members are concentrically assembled with a center connector 320 in a same manner as one in previous case by help of the spherical mold. The reamer built here has 4 cutting member arranged on the thin shell dome.

As another option of a reamer assembled by same type of the cutting element in the first case, referring to FIG. 5-2, most configuration of the cutting element are identical to the one in previous case, but each support member has a link mechanism, such as a link member 321 instead a receiving member 312 inwardly punched out from the thin shell wall. While all support members are inwardly bent toward the longitudinal axis and the link mechanisms 321 merge at the longitudinal axis and fasten together, so the reamer can be assembled by single cutting element alone. During assembling step of the reamer, each extending plane 348, as a transition portion between the support member 304 and the limb 310, is inwardly bent with the support member 304 together toward the longitudinal axis and by a bending angle 360 between the planar plane 346 the limb 310 and extending plane 348. In the meantime, the link member 321 is able to connect with other link members 321 on other sequential support member 304 together at the longitudinal axis. Those link mechanisms of the all support member 304 can be fastened together through various mechanical methods without the center connector. So the reamer is assembled by single piece of cutting element, instead two parts. A method of fastening the link members together can be selected from a self-locking, welding and other equivalent, if the link member is properly designed. Each size of the spherical concave mold used matches the spherical radius of the reamer to be formed. This key tool can also tests whether or not how each folded cutting element sits into the cavity and all cutting members intimately contact with the surface of the spherical mold, after the support members 304 are fastened together by welding.

Figure 6:
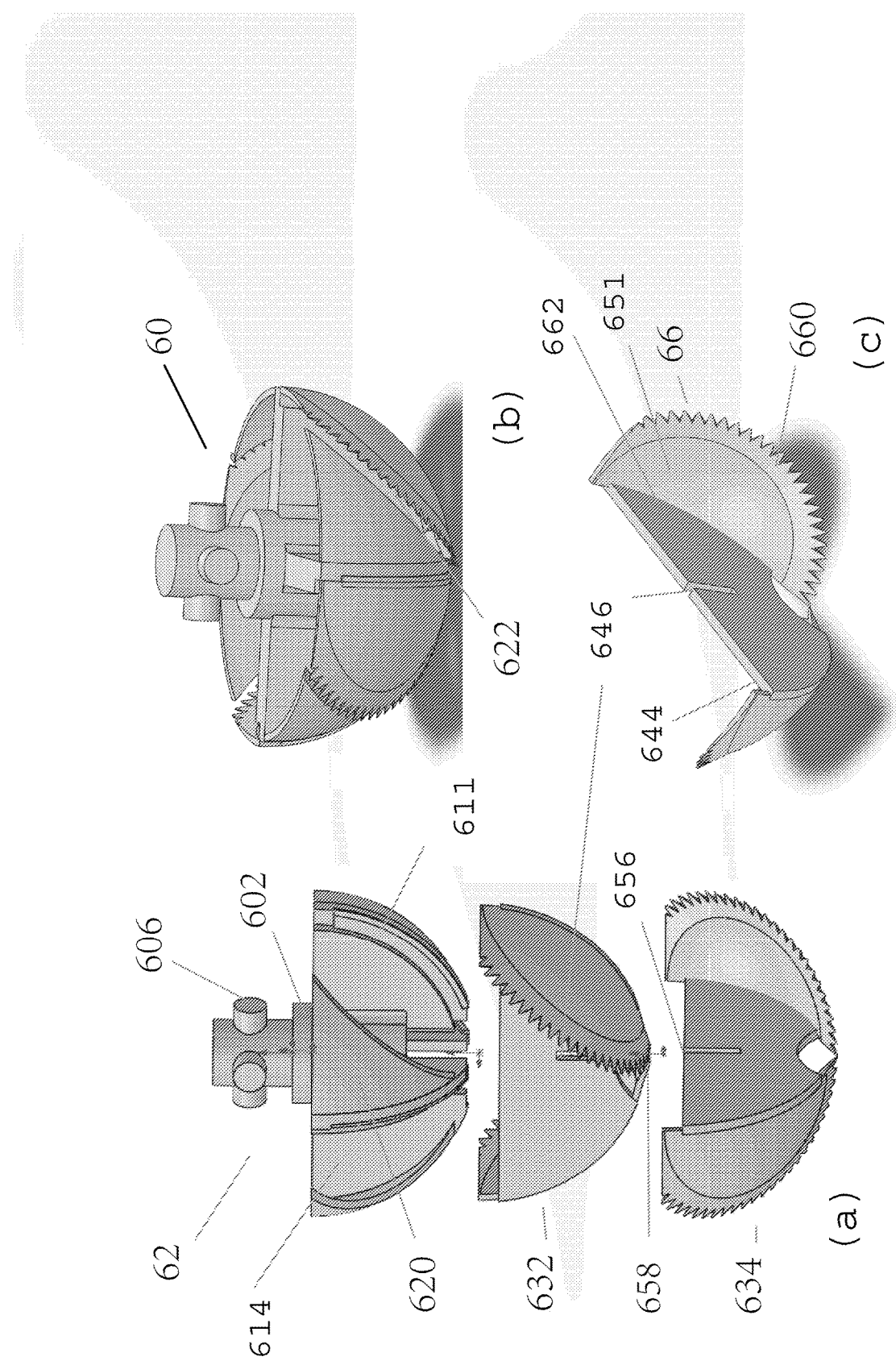
FIGS. 6(a)-(c) show detail features of Type II cutting element and reamer assembled by Type II cutting element.

As another option of a reamer assembled by a Type II cutting elements, as shown in FIG. 6, a reamer can be a reusable or a disposable reamer, 60. It basically comprises of one main frame or a center connector 62 having two holding sites or interfaces, because each Type II cutting elements here already has its own built-on geometrical and positional parameters.

The center connector 62 comprises a cylindrical portion, 602 along the longitude axis, having a coupling interface 606 on its upper distal end of the cylinder 602 for coupling with the driving shaft, and four quarter round plate 614, radically and symmetrically extended from the lower cylinder section 602. A perforation slot, called a receiving slot 611, vertically split the lower sections of the quarter round plate 614 and passes through the longitude axis. There are two receiving slots 611 orthogonally arranged each other at the longitude axis and form two receiving pockets for receiving each cutting element from its downside. The receiving slot 611 is downwardly opened toward the pole point and has a ceiling of the slot up to the spherical center and a wideness which matches the thickness of the cutting element. The receiving pocket can firmly hold or release two exchangeable Type II cutting elements 632, 634 by a holding mechanism (not shown). There also is a side thin shell wall for forming a collecting wall 620, which can be extended out from each trailing plate of the quarter round plate 644 in the counterclockwise direction. The thin wall of each main frame or the center connector has functions and configuration similar as one described in Embodiment I.

Referring to FIG. 6(c), each cutting element shown here comprise a connecting member 644, a half round plate, called a base portion here, and two support members, 651 located at each distal end thereof and bent by a first bending angle 662 from the connecting member 644 in opposite direction. A typical first bending angle 662 is 90 degrees. A circular cutting member is established around its circumferential trailing fringe and forms a cutting radius, a cutting plane a cutting center and a cutting axis, respectively. The support member is extended and bent in a manner that the cutting axis of a cutting member is tilted from the longitudinal axis by a given arm angle and the cutting center formed is away from the spherical center by the arm length. So the cutting members here possess all geometric and positional parameters, which are determined the spherical radius and cutting area of the reamer. A support member 651 between the connecting member 644 and cutting member 660 can also be a partial thin shell wall, called a transition wall, having a same radius as one in the frame or the center connector.

Referring to FIG. 6, the reamer formed comprises two linked cutting elements, an upper 632 and lower base portion, 634, which have a little different on its structure of base portion. A link mechanism, such as a center positioning slot, a receiving member 646, oppositely located on an upper 656 and lower base portion 658, respectively, in order that two plates orthogonally joint together along the longitudinal axis. The linked cutting elements can be slide into its center positioning slot 646 each other to form a united cutting element, which is ready to couple with the receiving slots 611 of the frame or the center connector 612, see FIG. 6(a).

As another option of assembling Type II cutting elements together through self-assembled method, referring to FIG. 9, a reamer 50 comprises three identical cutting elements 52 made by either conventional punching/stamping procedure from sheet metal or other methods up to its feasibility. Each cutting element comprises a support member 51 and one built-in, D-type cutting member, a cutting member 53. In detail, a shape of the support member 51 is a partial spherical thin shell for enhancing its strength and conducting force applied to the cutting member. The radius of the thin shell is not critical to the structure and is at least 2 mm in diameter less than the size of the surface to be cut. The cutting member 205 can also be either a D-type or C-type circumference cutting edge at a leading fringe 53 of the support member 51 and covers a cutting area at least from the equator to the polar point of the surface, even though its cutting edge might be less than half the circumference. Once three cutting elements are united as an integrated reamer, the location of each cutting member toward to the spherical center 214 is concentric and must be accurately defined by both geometric and positional parameters, respectively. Each cutting member 53 has a proper edge configuration and uniform contact angle toward the surface 220. 9999Optionally, there is also a side cutting edge within envelop of the notch and additional primary bevel on a side wall of the notch. Such detail texture in the part can be made by powder metallurgy or plastic molding or the like.

Referring to FIG. 9, the support member further comprises a link mechanisms, a connect member 54 and a second receiving member 56, such as a Tenon, on the trailing fringe and such as a mortise joint, on a position near the leading fringe 53 of the support member 51 for assembling with adjacent cutting element by either ultrasound heating, if support member 51 is made by plastic; or by metal welding method for a metal support member.

In addition, by help from using a hemispherical concave mold to position all cutting elements on the any desired location and orientation, different sizes of the reamer can be united by the same set of cutting elements through such the Tenon 54-Mortise 56 joint. The connecting member should have a certain allowance in both length and orientation in order to fit various size of the reamer format, if using method of "one for several" to assembly. In order to further strengthen the united pieces, an attachment, branched bars (not shown), can be either mechanically or releasablely affiliated the united reamer together in proper manner and at a proper position, the first receiving member 55 on the support member 51. It forms an interface for coupling with the driving shaft, Referring to FIG. 11, another alternative method used for assembling a reamer is the "self-assembly" method and "One for Several" methods combined. Two identical cutting elements 70 made by conventional procedure comprise a support member 82 having two built-in cutting members, a primary one 83 and secondary one 84. The major difference in comparison with one of the previous case is that the support member 82 further comprises another type of link mechanisms: an connecting member 90, as a Tenon, and a second receiving member or opening 91, such as mortise, located on different side of a center plane in mirror image manner. The center plane here is co-planed with or determined by the longitudinal axis and the cutting axis of each cutting element. The connecting member 90 having an ached ribbon shape 728 is extended from a lower portion of the inner surface of the support member 82 and is curved at its distal portion of the ribbon. An arched portion 728 of the connecting member 90 has a shape to match the swinging track of the cutting element to allow the cutting elements free swing around the polar point. Two identical cutting elements 70 are self-assembled together through their link mechanisms 90, 91 and fastened by welding. As a skilled person in the art knows, the swinging point is the polar point of the spherical surface to be cut. Referring FIG. 10(b), A variation of the spherical radius of the reamer built can be fulfilled by changing the swinging angle from one to another, as shown in FIGS. 9(b) and (c), respectively.

By help of the tooling mold which has a same requirement in previous case discussed, the different spherical radius of the reamer are able to be accurately assembled by same set of cutting elements through such the Tenon—mortise joints on the support member. The ribbon connecting member are welded or fastened with the counterpart of the support member from the outside to permanently fix their positions/structure. The cutting elements linked are further strengthened by that the center connecter 730, two crossbars fastens with the first receiving member 89 during assembling, near the equator circle in order to couple with the driving shaft. The dimension of the mold used determines the spherical radius of the reamer desired. Referring to FIG. 11(b, c), by swinging the cutting plane of two cutting elements assembled around the polar point in different swing angle, the spherical radius of the reamer varies from first one to the second one.

Alternatively, the cutting element 70 can be also made by disposable materials (plastic) through insert molding injection (as mentioned above) and comprises a support member 82, having a plastic body and cutting members (Type III cutting element as shown in FIG. 4) made by metal sheet, as inserting cutting member of the support member 82. The cutting members are united with the support member 82 together by the insert molding injection as a single piece and have identical configurations as one of the cutting element made by metal sheet in previous description. Such cutting elements are able to be self-assembled in various fashions as described above by ultrasound heating to form a single reamer with different spherical radius.

Figure 7:
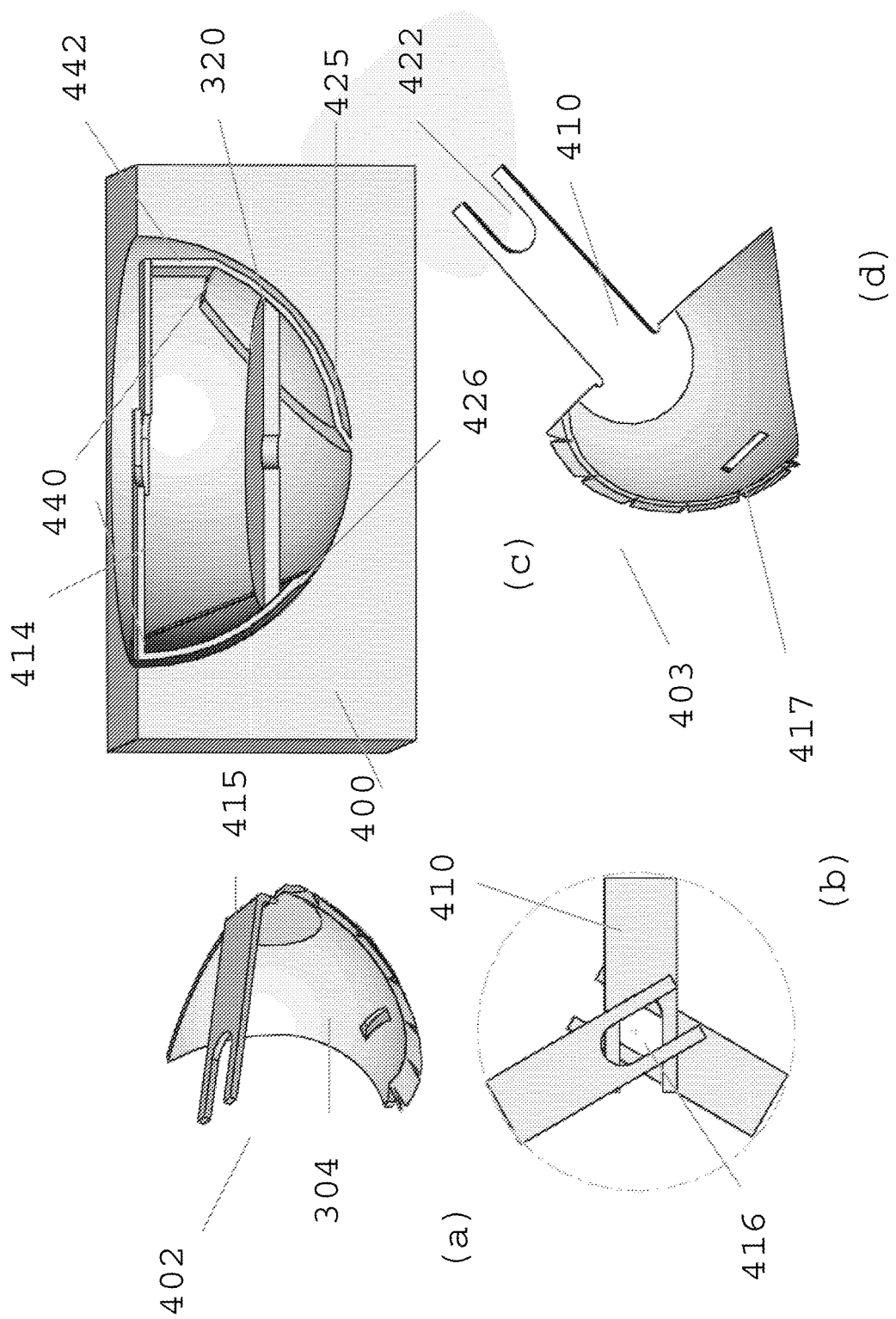
FIG. 7(a)-(d): (a, d) show a folded and unfolded cutting elements, respectively; (b) shows top view of 3 elongated connecting members assembled, which forms a center hole; (c) shows a cross section of that two cutting elements sit into a spherical mold 400, are tilted by different arm angle and a manner to assembling a reamer with different spherical radius.

Referring to FIG. 7, another alternative method for assembling the reamer is used by combining the "self-assembly" method and "overlapping" methods. A folded or an unfolded cutting element 403 or 402 has shown in FIG. 7(a, d), respectively. A cutting element is initially made by conventional sheet-metal procedure to form all necessary features on the support member 304 and have a specific positional relationship as described in previous case, except that a different feature of the unfold connecting member 410 is a part of a link mechanism, which is elongated by certain distance and has a straight slot 422 having one opened distal end of the connecting member 410. Referring to FIG. 5-1, and FIG. 7, particularly, the preset parameters include: the cutting axis 212, the longitudinal axis 200 and a center line of the two edges of the limb 310 are in common plane. The cutting plane 230 of the cutting member 205 forms a specific angle toward the plane of limb 310. The specific distance or arm (limb) length from upper edge 308 to the longitudinal axis 200 should be long enough and satisfy the geometric rule. Referring to FIG. 7(c), as an independent part, the cutting element here is able to assembly a reamer with different spherical radius. In order to do so, a length allowance of connecting member 410 and opened slot 422 must have enough length for satisfying requirement of both its horizontal extending section 415 and vertical section 442 of the connecting member 410.

Referring to FIG. 7(c), as example, two cutting member 425 and 426 of the cutting elements have intimately contacted with surface of the spherical cavity, respectively. Each cutting member covers different latitudes of the spherical surface. Between the upper and lower latitudes covered, there is an overlapped portion. In order to do so, each connecting member 410 is bent in different area 442 and by different bending angle 440 to split connecting member 410 to horizontal extending section 415 and vertical section 442. Along with increasing the spherical radius of the reamer, except simultaneously increasing the arm length, a cutting axis of the upper cutting member 426 turns further to equator 202 around the spherical center 214 and the cutting axis of the lower cutting member 425 turns oppositely to polar point 203 of the spherical surface. The proper bending angle 440 and a height of the extending area 420 determine the position and orientation of each cutting member toward the longitudinal axis and a manner how two limbs 414 to meet each other during assembling them together.

Up to the spherical radius of reamer required, the cutting element 403 with a same unfolded format is inwardly folded at specific position of the connecting member 410 and by a specific bending angle 440. For each folded cutting element 402, the length of horizontal extending section 415 and vertical section 442 of the connecting member 410 might have a different. While all parts sits into the spherical concave mold 400, first all cutting members intimately contact with the surface of the cavity, then all connecting members 410 can be horizontally stacked up along the direction of the longitudinal axis and equally spaced apart from each other by certain angle interval (180 120 or 90 degree angle). Referring to FIG. 7(b), assuming the reamer assembled by three cutting elements, when all 3 stacked connecting members 410 symmetrically merge together by an interval of 120 degree angle, it forms a center hole 416 (from a top view). A structure assembled by 3 folded cutting elements 402 is further strengthened by coupling a center connector 320 and a receiving member 417 in the lower portion of each support member 304 together. One cutting element can be assembled by combining other cutting elements with a different folding format to have different spherical radius of reamer. Up to the reamer assembled, each cutting plane of the cutting member has an arm angle and arm length corresponding to the spherical radius of the reamer. The reamer formed in this manner has a similar structure and function as one described in previous options. From point of view of a skilled person in the art, any detailed features or factors can be added on the reamer in order to strengthen the structure in term of enhancing its reliability and durability without leaving the sprite of the present invention.

By reviewing all examples of self-assembling a reamer from Type II cutting element above, the common feature is that all support members are self-assembled by fastening the link mechanisms together in a manner with or without the center connector. There are several manners of building the link mechanism on support members. How the link mechanism builds on the support member depends upon the assembling method used. The link member can be in paired and mirror image manner and in positions extended from upper/lower portion, or near leading/trailing fringe, or each side of the center plane of the support member, respectively. A manner of fastening them together can be self-linked or linked together with an accessory, such a center connector.

Embodiment II

Referring to FIG. 13, a reamer, more preferred as a disposable reamer, not limited, is assembled by the Type III cutting members or element and comprises a disposable thin support member or reamer shell, or a center connector, 902 having a holding member 916 and at least two cutting elements/members 904 with identical configuration. The reamer shell 902 is a partial hemispherical thin shell wall 910 having a radius 1 or 2 mm less than the cutting radius of the reamer formed and comprises a plurality of holding member 920, a corresponding slot opening 914 nearby, as a tunnel/passage between an exterior hemispherical surface into an internal chamber, and two crossbars 916 for coupling with the driving shaft located near the equator. The holding member 912 symmetrically are arranged with a respect to the longitudinal axis and comprise an arched receiving groove 920 along the spherical fringe of the slot opening 914, which matches a corresponding radius of the cutting member 904 to be inserted. An orientation and a configuration of the receiving groove 920 is defined by dimensional and positional parameters of the corresponding cutting member 904, and also determine the spherical radius of the reamer, once the cutting member 904 is imbedded into the groove. The thin reamer shell can be made by materials selecting from a group of metal, ceramic and disposable materials or others. The support member 924 in the Type III cutting element is optional. Its function can be a positioner of the cutting member 922 for conveniently locating them during insert molding.

In other embodiment, alternative disposable reamer, referring to FIG. 4, a type III cutting element 61, as an insert cutting element, comprises two identical cutting members 68 symmetrically linked together by a support ribbon 63 with respect to the longitudinal axis. FIG. 4(a) has shown the cutting element in the 2-D shape punched from thin sheet metal. The cutting members would face opposite cutting direction, while imbedded. An orientation and a position of the cutting members are regulated by a bending fashion 67 of the support ribbon 63 and further by a receiving groove in the reamer shell. The support ribbon 61 comprises three sections: a center section 64 and two symmetrical side arm sections 65. The cutting member 68 located at distal end of each side arm section 65. There is a bending angle 69 between edges of the center and the side arm section, which can correspond to the arm angle formed of the cutting member (determined by geometry rule), while the cutting member 68 is imbedded in the corresponding pocket of the reamer shell. The arm section 65 counterclockwise is bended 90 degrees from the center section 64. A distance between the center of the corresponding bending point 67 and the spherical center correlates to the arm length formed of the cutting element. The cutting diameter of the cutting member is curved by the radius of the groove curvature of the thin reamer shell, while it is imbedded. The disposable reamer is built, while the cutting element 68, referring to FIG. 4(c), is imbedded with the thin reamer shell by insert molding injection or similar.

Embodiment III

Referring to FIG. 3, the type I cutting element used here comprises two sections of the cutting member are: 1) a primary cutting section 372 is on a leading side of the circumferential edge and is able to cover a cutting area from equator 202 to pole 203 of the hemisphere to be cut and 2) a secondary cutting section 374 is on a trailing side of the circumferential edge and is able to cover a cutting area from equator 202 to intermedia area 376 near pole, but not polar area, of the hemisphere. On the support member 304, there are detailed features: a positional hole 367 and locking holes 369.

Referring to FIG. 12, the reamer 70 comprises three mounting site 710 of the frame or the center connector 72. The three mounting sites 710 can have a same symmetrically structure having preset arm angle and preset arm length or asymmetrical one, if the preset arm angle is different in order that cutting elements 76 cover different cutting area. The frame or the center connector 72 comprises three symmetrically branched bars 722 linked with the mounting site 710 for further coupling to the driving shaft and three collecting wall 720 extended from the corresponding mounting site 710, respectively. The exchangeable cutting element 76 is able to releasably couple with the positional slot, or groove 705 of the mounting surface 712 and be locked by a snap-fit pin. Each cutting element 76 comprises a less half circumferential cutting edge 740 extended from a half round support member 78 and positional holes 742. While the cutting element 76 positioned, all positional parameters must satisfy the geometric rule discussed above. The collecting wall 720, a side thin shell wall, has a radius 1-2 mm smaller than the spherical radius to be cut and counterclockwise extended out from the trailing edge of each mounting site 710. The trailing edge of the thin wall leaves at least 3-5 mm gap 724 from the adjacent cutting member, while it is positioned. The collecting wall of each mounting site 710 has a function of: 1) a pocket of collecting debris during cutting the surface and 2) forming a fine cutting gap with a primary cutting edge of the cutting element nearby, in order to prevent over-cutting the surface, like a function of one adjusting a gap of carpenter plane.

Figure 10:
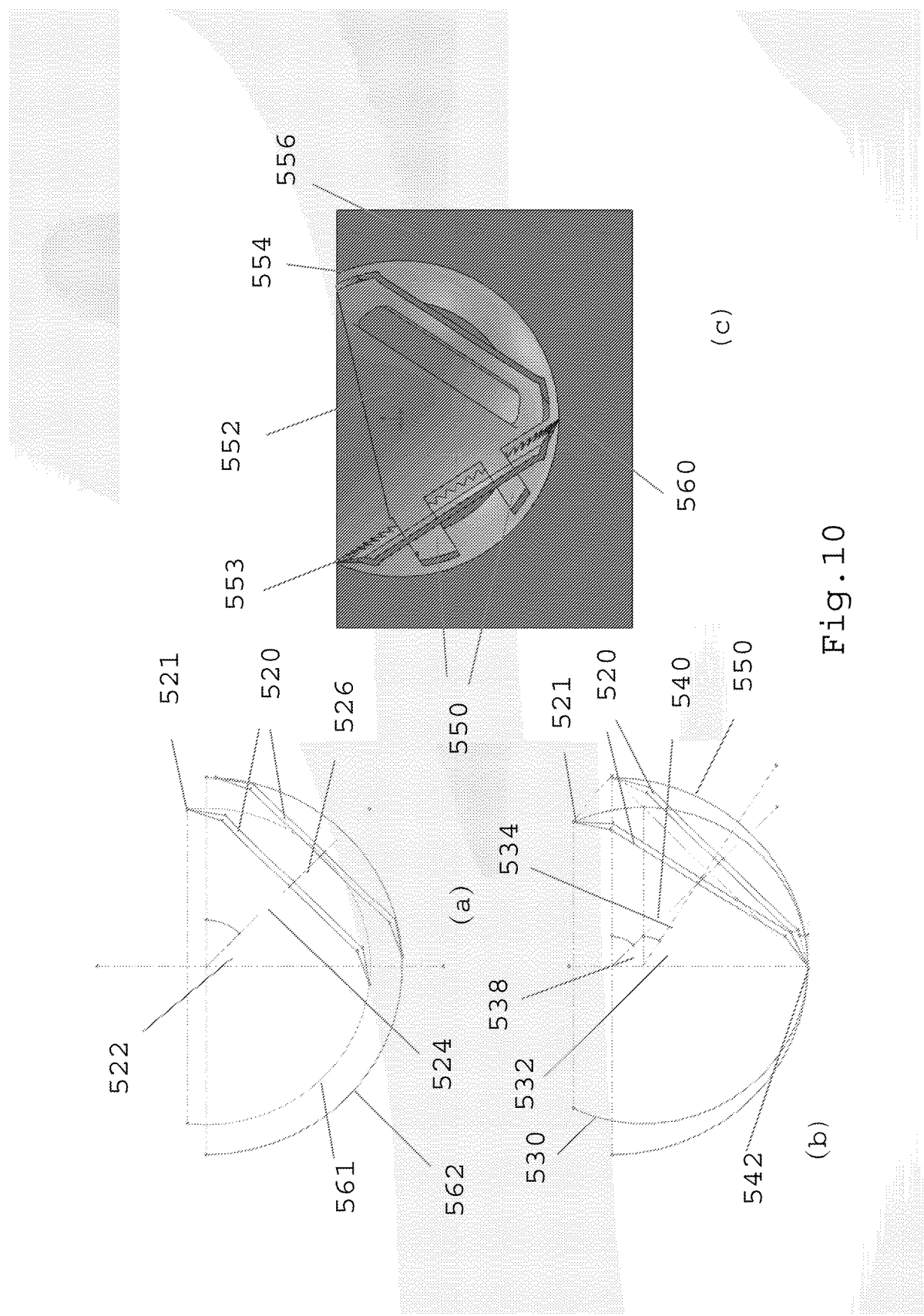
FIG. 10 shows the principle of "one size cutting element for assembling reamer with different spherical radius, and the method for assembling the reamer. (a) shows a fixed angle method; (b) shows a varying angle method; (c) shows positioning the cutting elements by a spherical concave mold.

Referring to FIG. 10, the Type I cutting element can be assembled by the "One for Several" methods with a help of a hemispherical concave mold, if the corresponding frame or the center connector is available.

In view of any possible embodiments in which the principles of the disclosed invention above may be applied, it should be perceived that the illustrated embodiments are only preferred examples of describing the invention and should not be taken as limiting the scope of the invention.

What we claim:

1. A hemispherical reamer being attachable to a driving shaft and rotatable around a longitudinal axis and having a spherical cutting radius and a spherical center comprises:
   a) a plurality of limbs being equally spaced apart from each other and symmetrically extending from the longitudinal axis,
   b) a support member extending from a distal end of each limb and further comprising at least one link mechanism established on the support member and
   c) at least one circular cutting member at least extending from edge of the support member and established a circumferential cutting edge thereon having a cutting radius, a circular cutting center and a virtual circular plane of the cutting edge thereof;
      wherein each support member is inwardly bent toward the longitudinal axis and symmetrically coupled together with adjacent support members by the link mechanisms thereof for assembling the reamer, by which the circular plane is perpendicular to the spherical cutting radius and is titled away from the longitudinal axis to form an arm angle between the longitudinal axis and a cutting axis of each cutting member and the circular center of the cutting member is spaced apart from the spherical center in a distance defining an arm length between the spherical center and the cutting center of the cutting member along the cutting axis, respectively; and wherein the arm length and the cutting radius of the cutting member determine the spherical cutting radius of the reamer.

2. The hemispherical reamer of claim 1, wherein each cutting member comprises a primary bevel and a plurality of notches distributed on a cutting edge and a bending angle or a contact angle between the edge and the surface to be cut.

3. The hemispherical reamer of claim 1, wherein a cutting area to be cut by each cutting member is determined by the arm angle thereof if the cutting radius of the cutting member remains same.

4. The hemispherical reamer of claim 1, wherein the support member comprises either a partial spherical thin shell wall or a dish-like wall or others and their combinations.

5. The hemispherical reamer of claim 1, wherein the link mechanisms from at least two adjacent cutting elements are symmetrically coupled together, while each support member is inwardly bent from the limb and toward the longitudinal axis for assembling the reamer.

6. The hemispherical reamer of claim 1, wherein the limbs are a holding interface for communicating the driving shaft, while support members are inwardly bent toward the longitudinal axis and coupled to assemble the reamer.

7. The hemispherical reamer of claim 1, wherein the link mechanism of each support member is coupled with a center connector together, while each support member is inwardly bent toward the longitudinal axis for assembling the reamer.

8. A hemispherical reamer being attachable to a driving shaft and rotatable around a longitudinal axis and having a spherical cutting radius, a spherical center and a polar point thereof comprises a plurality of cutting elements, each comprising: a) at least one circular cutting member extending from a circumferential leading fringe of a support member and having a cutting radius, a cutting center and a virtual circular plane of a cutting edges, respectively; and b) a plurality of link mechanisms established on the support member for symmetrically coupling with the support members of sequential cutting elements together around the longitudinal axis for assembling the reamer, by which each circular plane is perpendicular to the spherical cutting radius and titled away from the longitudinal axis to form arm angle between the longitudinal axis and a cutting axis of each cutting member and the cutting center is spaced apart from the spherical center in a distance defining an arm length between the cutting center of the cutting member and the spherical center along the cutting axis, respectively, and wherein the arm length and the cutting radius of the cutting member determine the spherical cutting radius of the reamer assembled.

9. The hemispherical reamer of claim 8, wherein the link mechanism comprises at least one connecting member and/or one receiving member or link member established in paired and mirror image manner and at either an upper/lower portion or a leading/trailing fringe, or each side of a center plane of the support member, respectively; and wherein the center plane of the cutting element is determined by the longitudinal axis and the cutting axis of each cutting element.

10. The hemispherical reamer of claim 8, wherein each cutting member comprises a primary bevel and a plurality of notches distributed on cutting edge and a bending angle or a contact angle between the edge and the surface to be cut.

11. The hemispherical reamer of claim 8, wherein a cutting area or a cutting section of the cutting member is determined by the arm angle thereof, respectively, if the cutting radius of the cutting member remains same.

12. The hemispherical reamer of claim 11, wherein the spherical radius of the reamer is varied by an assembling method selected from groups of a method: a) by varying the arm length at same arm angle of each cutting element, b) varying the arm length, but differently tilted arm angle of each cutting element and c) varying a swinging angle between the longitudinal axis and the circular plane of each cutting element around the polar point, if the cutting radius of all cutting members remains same.

13. The hemispherical reamer of claim 12, wherein the link mechanisms couple all cutting elements together for assembling the reamer, at which each cutting member possesses a position defined by the arm length and/or the arm angle, which is different from others in order to assemble a reamer having the corresponding spherical radius and/or cutting area being different from others, respectively.

14. The hemispherical reamer of claim 8, wherein the cutting element comprises a secondary circumferential cutting member established at area between the leading and the trailing fringes of support member and having same cutting radius as the ones of the cutting member on the leading fringe.

15. The hemispherical reamer of claim 8, wherein the cutting element further comprises a plurality of curvature grooves on a partial spherical shin shell wall thereof for positioning a ribbon cutting member in a proper format and orientation with a respect to the longitudinal axis and the spherical center, which are characterized by arm angle and arm length, respectively.

16. The hemispherical reamer of claim 8, wherein the support member comprises at least a receiving interface for being able to communicate with the driving shaft, while the reamer is assembled by coupling all cutting elements together.

17. A hemispherical reamer being attachable to a driving shaft and rotatable around a longitudinal axis and having a spherical radius, a spherical center and a polar point thereof comprises: a) a center connector comprising a plurality of interfaces being equally spaced apart from each other and having a desired position and orientation toward the spherical center and the longitudinal axis; and b) a plurality of cutting elements comprising a support member and at least one circular cutting member extending from a circumferential edge of each support member and having a cutting radius, a cutting center and a virtual circular plane; wherein each cutting element or each cutting member is positioned on the corresponding interface of the center connector, while assembling the reamer, by which the circular plane of the cutting member is perpendicular to the spherical cutting radius and titled away from the longitudinal axis to form an arm angle between the longitudinal axis and a cutting axis of the cutting member and the cutting center thereof is spaced apart from the spherical center by a distance defining an arm length between spherical center and the cutting center of the cutting member along the cutting axis, respectively; and wherein the arm length and the cutting radius of the cutting member together determine the spherical radius of the reamer assembled.

18. The hemispherical reamer of claim 17, wherein the center connector further comprises a hemispherical thin shell, a plurality of curvature grooves of the interface established along the surface of the shell, a plurality of openings being adjacent to each cutting plane of the cutting member to form a narrow passage extending from the exterior hemispherical surface into the internal chamber of the shell and at least one holding member for communicating with the driving shaft.

19. The hemispherical reamer of claim 18, wherein the hemispherical thin shell is made by a molded plastic substrate and has a plurality of holders established on an equator circumference of the shell for communicating with the driving shaft; and wherein each groove is orientated toward the longitudinal axis and the spherical center for positioning a ribbon cutting member.

20. The hemispherical reamer of claim 17, wherein each cutting member comprises a primary bevel and a plurality of notches distributed on cutting edge and a bending angle or a contact angle between cutting edge and the surface to be cut.

21. The hemispherical reamer of claim 17, wherein a cutting area of each cutting member is determined by the arm angle thereof while the cutting radius of the cutting member remains same.

22. The hemispherical reamer of claim 17, wherein the spherical radius of the reamer is varied by an assembling method selected from a group of methods of: a) varying the arm length at same arm angle of each cutting member, b) varying the arm length, but differently tilting arm angle of each cutting member and c) varying a swinging angle between the longitudinal axis and the circular plane of the cutting member around the polar point, if the cutting radius of all cutting member remains same.

23. The hemispherical reamer of claim 22, wherein each cutting element or cutting member positions with the interface together for assembling the reamer, at which each cutting member possesses a position characterized by the arm length and/or the arm angle being different from each other in order to the reamer having the corresponding spherical radius and/or cutting area being different from others, respectively.

24. The hemispherical reamer of claim 17, wherein the support member has a configuration selected from the groups of a dish-like, an annulus, a cylinder, a partial circumferential edge, a ribbon and others or their combinations.

* * * * *